United States Patent
Baxter et al.

(10) Patent No.: US 9,526,863 B2
(45) Date of Patent: Dec. 27, 2016

(54) DEVICES AND METHODS FOR PERFUSION THERAPY

(71) Applicant: NEURONAL PROTECTION SYSTEM, LLC, Chattanooga, TN (US)

(72) Inventors: Blaise Baxter, Signal Mountain, TN (US); Thomas Devlin, Signal Mountain, TN (US); Christian Devlin, Signal Mountain, TN (US); Paul J. Fitzpatrick, Marietta, GA (US); Dirk V. Hoyns, Jackson, GA (US); Charles Rex Teeslink, Augusta, GA (US)

(73) Assignee: NEURONAL PROTECTION SYSTEM, LLC, Chattanooga, TN (US)

( * ) Notice: Subject to any disclaimer, the term of this patent is extended or adjusted under 35 U.S.C. 154(b) by 204 days.

(21) Appl. No.: 14/094,758

(22) Filed: Dec. 2, 2013

(65) Prior Publication Data
US 2014/0155862 A1    Jun. 5, 2014

Related U.S. Application Data

(63) Continuation-in-part of application No. 12/702,245, filed on Feb. 8, 2010, now Pat. No. 8,622,992.

(60) Provisional application No. 61/150,783, filed on Feb. 8, 2009, provisional application No. 61/263,790, filed on Nov. 23, 2009.

(51) Int. Cl.
*A61M 25/00* (2006.01)
*A61M 5/142* (2006.01)
*A61B 17/22* (2006.01)

(52) U.S. Cl.
CPC .......... *A61M 25/0054* (2013.01); *A61B 17/22* (2013.01); *A61M 5/142* (2013.01); *A61M 25/007* (2013.01); *A61B 2017/22044* (2013.01); *A61B 2017/22084* (2013.01); *A61B 2017/22094* (2013.01); *A61M 2025/0079* (2013.01)

(58) Field of Classification Search
CPC ........ A61M 1/00; A61M 25/10; A61M 27/00; A61M 31/00; A61M 37/00; A61M 39/00; A61M 25/0054; A61M 25/007; A61M 2025/0079; A61M 5/142; A61B 17/22; A61B 2017/22044; A61B 2017/22084; A61B 2017/22094
See application file for complete search history.

(56) References Cited

U.S. PATENT DOCUMENTS

| 5,626,564 A * | 5/1997 | Zhan | A61M 25/007 604/164.01 |
| 5,830,181 A * | 11/1998 | Thornton | A61M 25/104 604/102.01 |
| 6,436,087 B1 * | 8/2002 | Lewis | A61B 17/22 128/898 |

(Continued)

FOREIGN PATENT DOCUMENTS

| DE | WO 2008100790 A2 * | 8/2008 | ........ A61M 25/0054 |
| WO | WO 2009126747 A1 * | 10/2009 | ....... A61B 17/12022 |

*Primary Examiner* — Tatyana Zalukaeva
*Assistant Examiner* — Benjamin Klein
(74) *Attorney, Agent, or Firm* — Soody Tronson; STLG Law Firm

(57) ABSTRACT

Devices, methods, and assemblies for perfusion therapy including cerebral perfusion therapy such as those for use in the treatment of acute ischemic stroke. The treatment includes delivery of blood to or about the vicinity of a thrombus site.

18 Claims, 19 Drawing Sheets

(56) References Cited

U.S. PATENT DOCUMENTS

| | | | |
|---|---|---|---|
| 6,537,241 B1 * | 3/2003 | Odland | A61M 1/1678 604/264 |
| 6,569,147 B1 * | 5/2003 | Evans | A61B 17/22 604/509 |
| 6,602,241 B2 * | 8/2003 | Makower | A61B 17/12109 604/103.01 |
| 6,605,074 B2 * | 8/2003 | Zadno-Azizi | A61B 17/22 604/507 |
| 6,790,204 B2 * | 9/2004 | Zadno-Azizi | A61B 17/22 604/507 |
| 6,945,978 B1 * | 9/2005 | Hyde | A61B 17/00234 606/142 |
| 7,235,264 B2 * | 6/2007 | Neu | A61K 33/00 128/203.12 |
| 7,427,287 B2 * | 9/2008 | Turovskiy | A61B 17/3417 604/164.01 |
| 7,700,135 B2 * | 4/2010 | Neu | C04B 22/0053 424/600 |
| 8,641,697 B2 * | 2/2014 | Partlett | A61M 25/0009 604/523 |
| 8,831,741 B2 * | 9/2014 | Griswold | A61M 25/0074 604/508 |
| 2002/0169473 A1 * | 11/2002 | Sepetka | A61B 17/12022 606/200 |
| 2005/0288631 A1 * | 12/2005 | Lewis | A61B 17/22 604/98.01 |
| 2006/0149187 A1 * | 7/2006 | Bertolero | A61M 25/003 604/96.01 |
| 2008/0058758 A1 * | 3/2008 | Ranchod | A61M 25/007 604/508 |
| 2008/0058759 A1 * | 3/2008 | Makower | A61M 25/0084 604/509 |
| 2008/0200946 A1 * | 8/2008 | Braun | A61M 25/0054 606/198 |
| 2010/0174183 A1 * | 7/2010 | Schwartz | A61M 25/007 600/433 |
| 2011/0087261 A1 * | 4/2011 | Wittkampf | A61B 17/3478 606/185 |

* cited by examiner

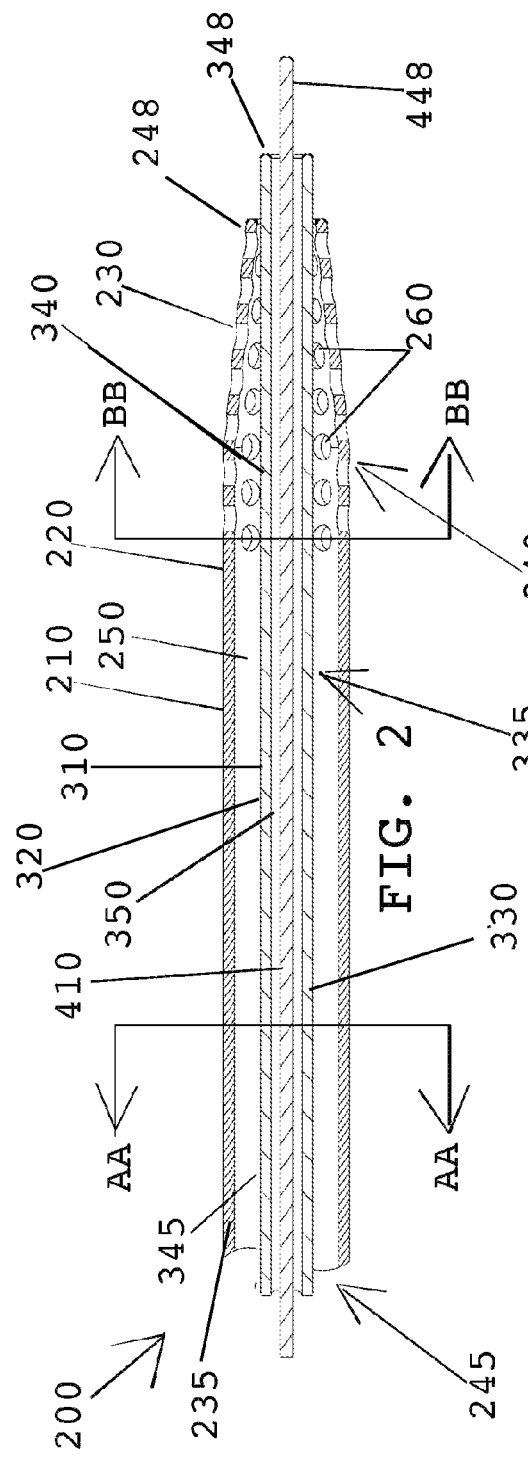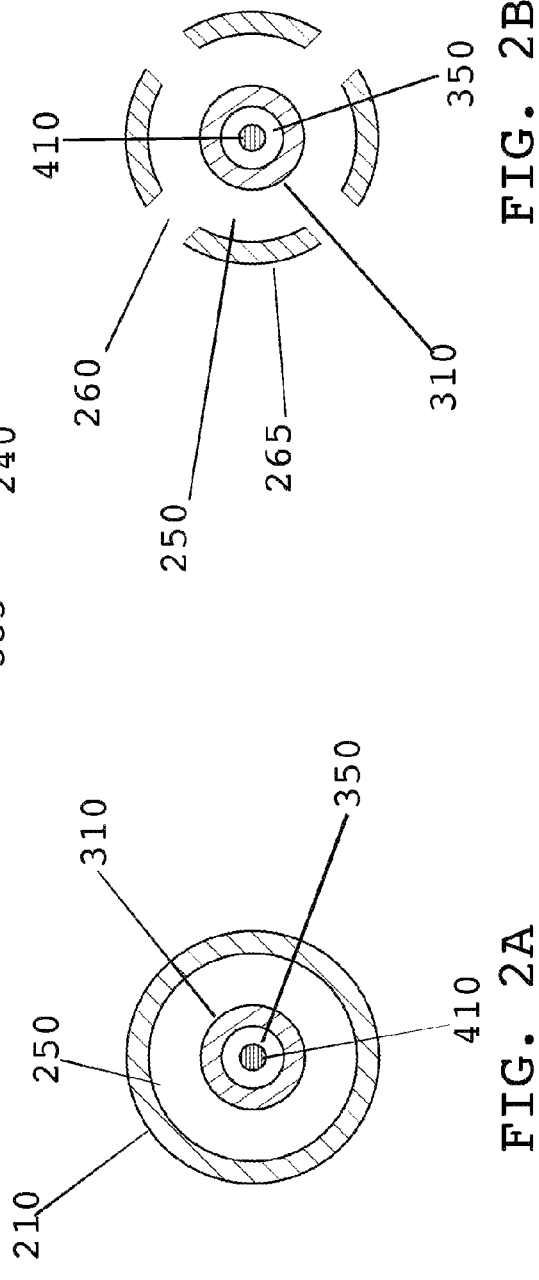

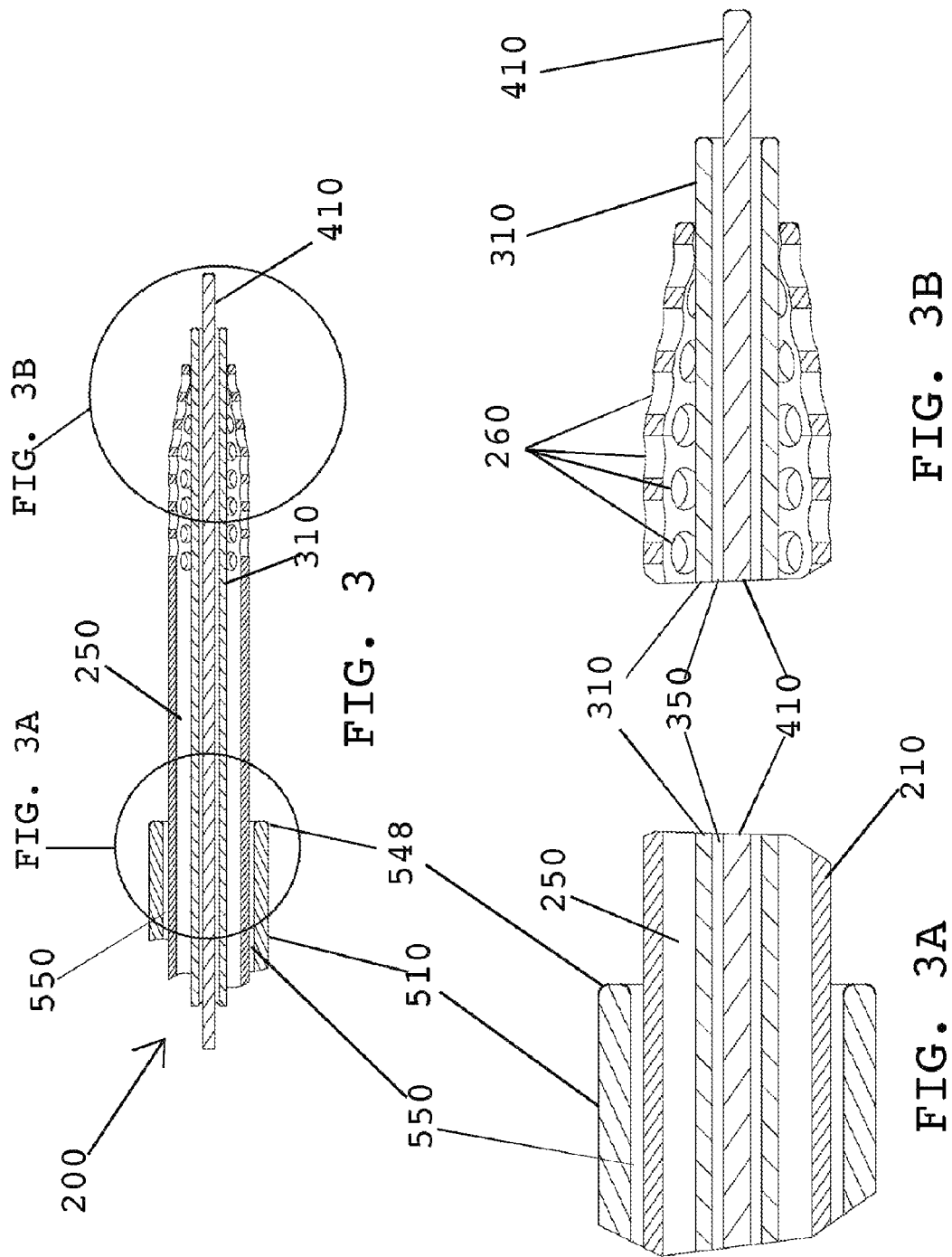

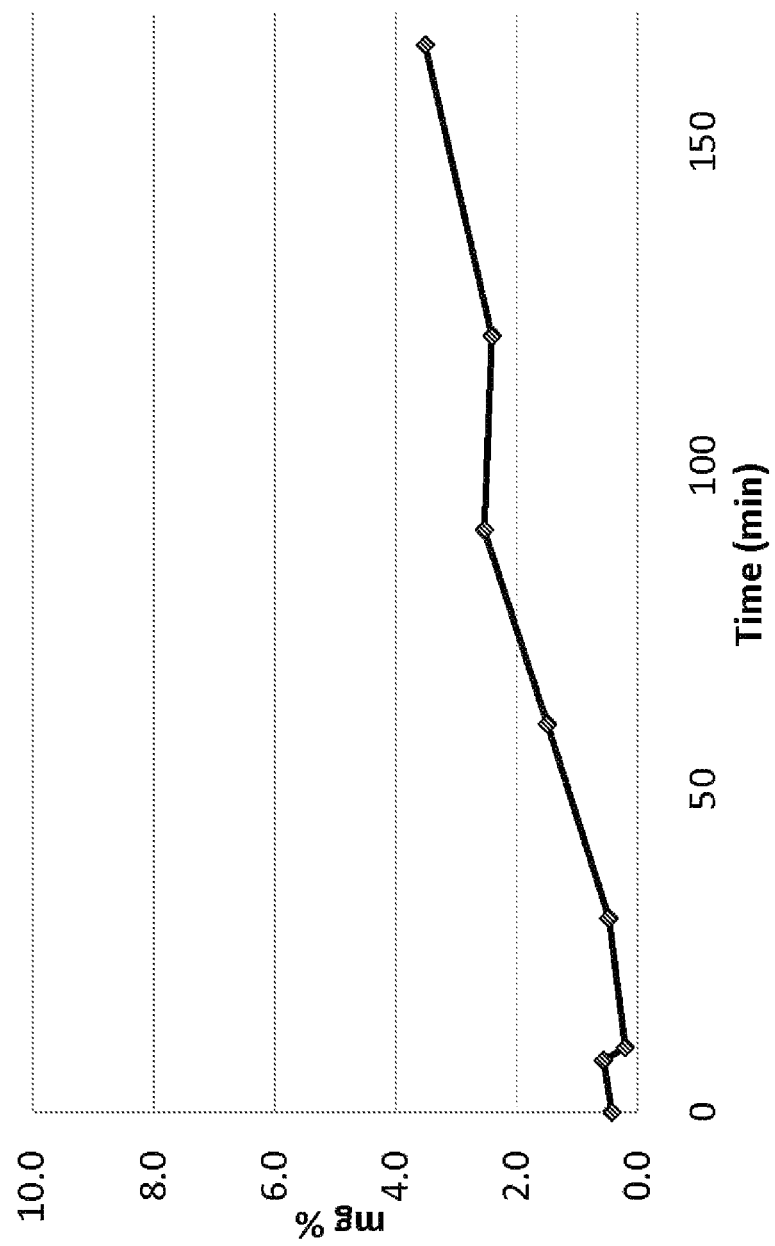

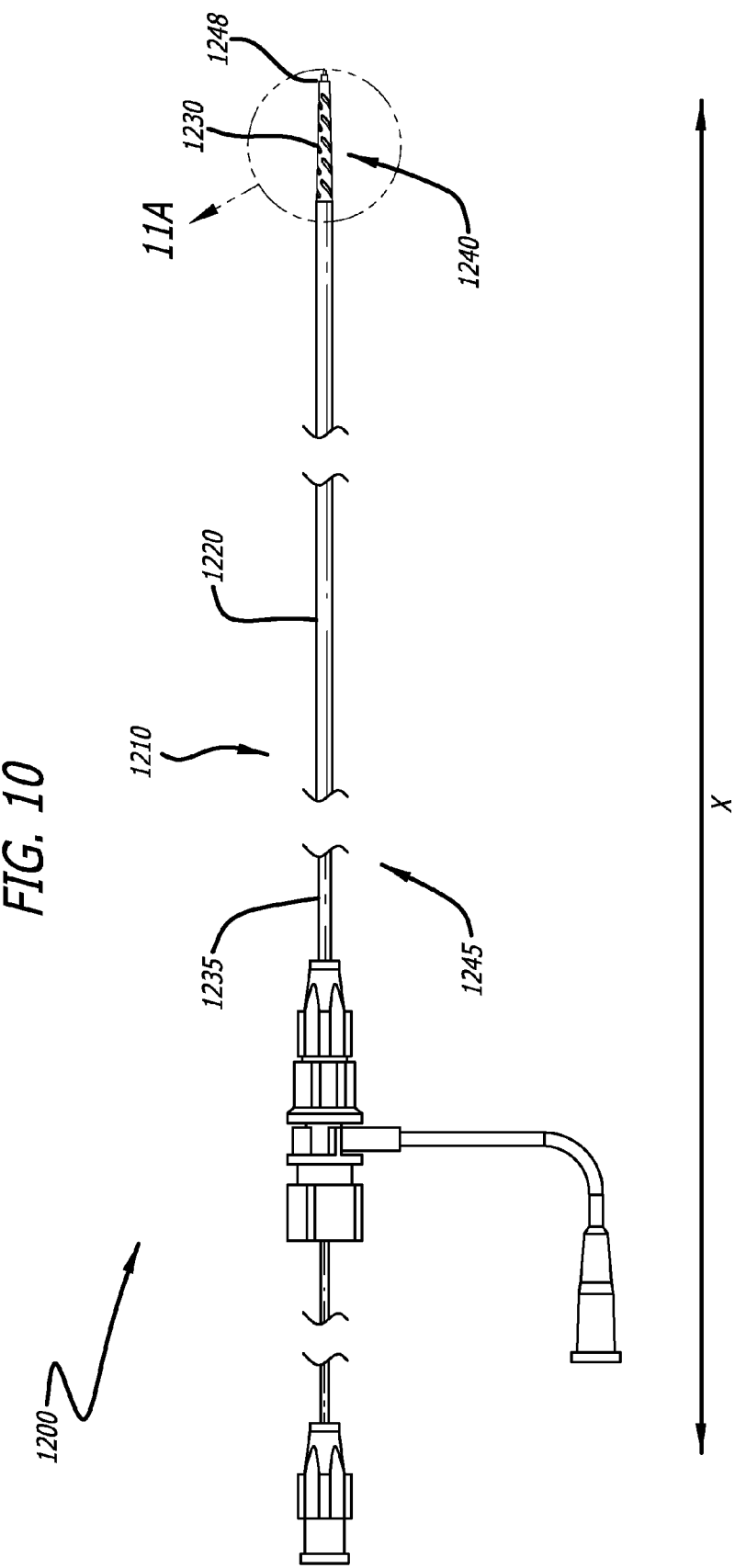

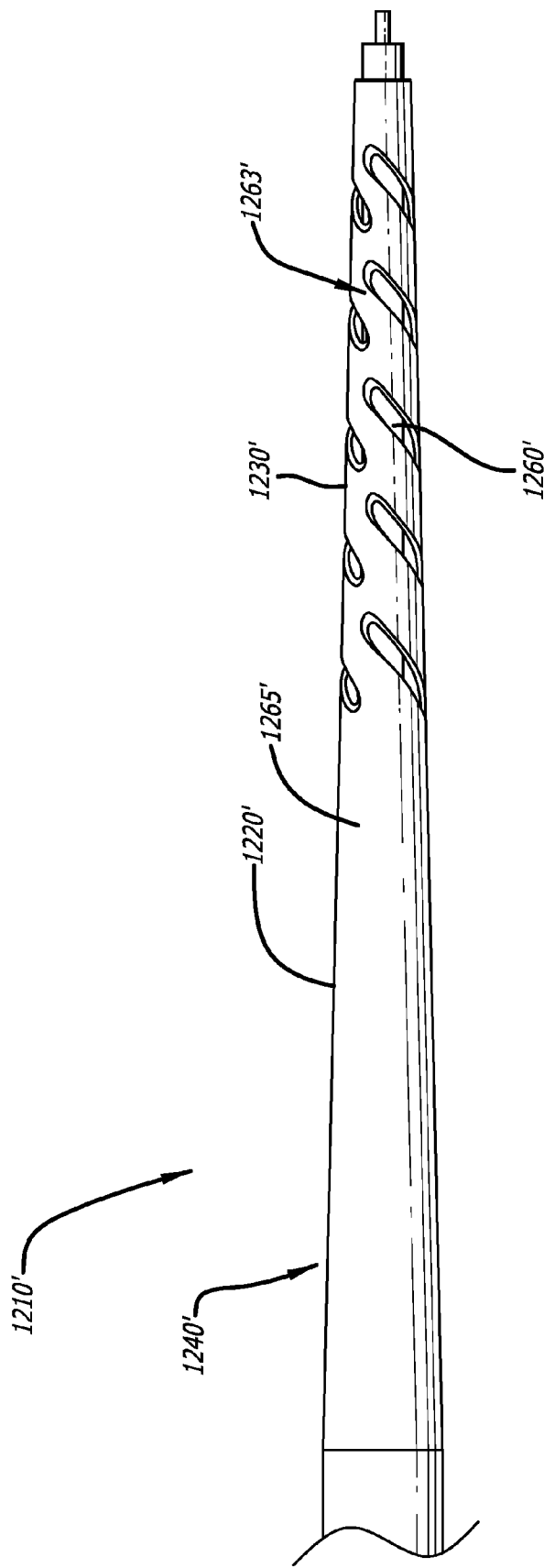

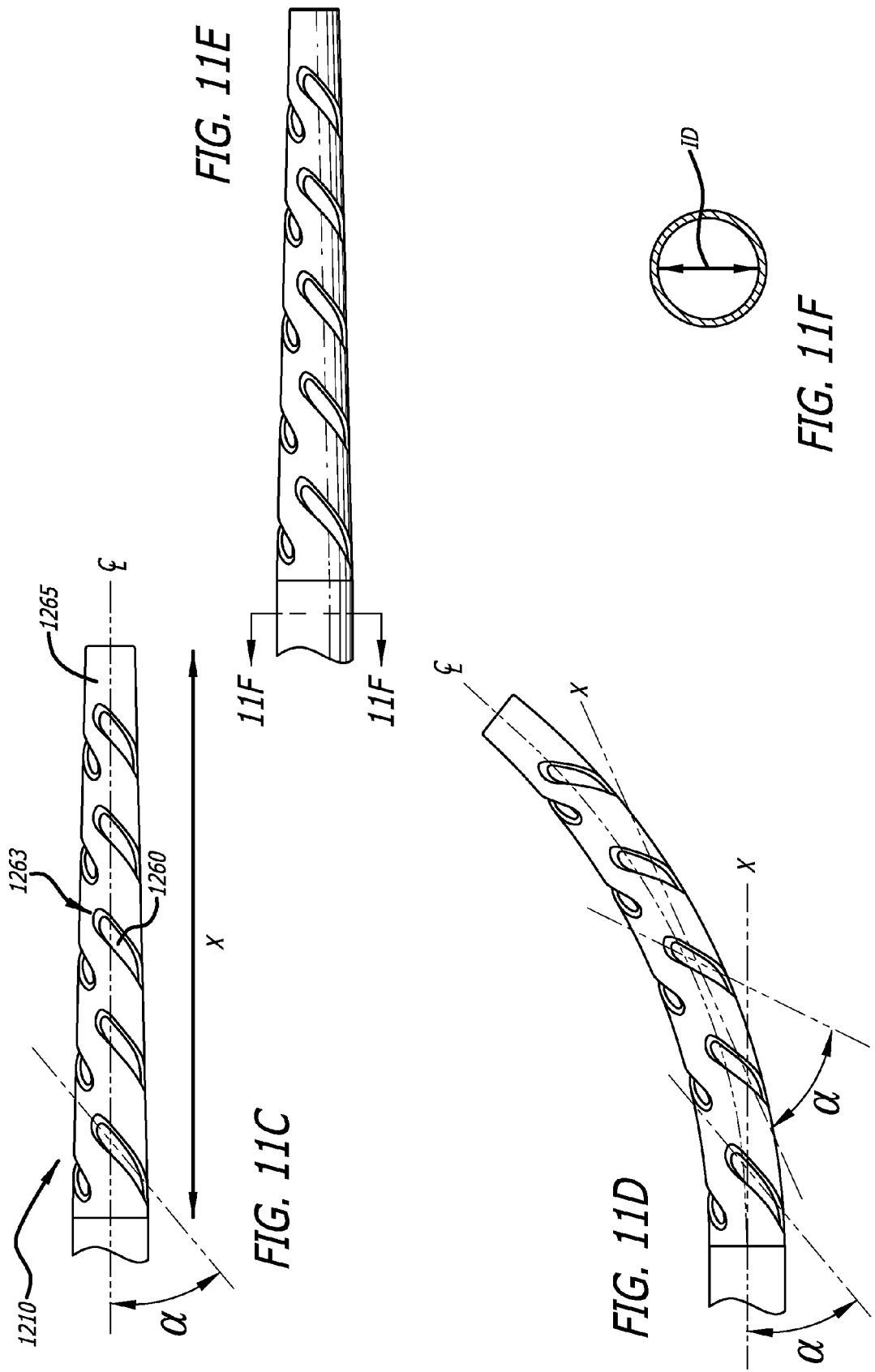

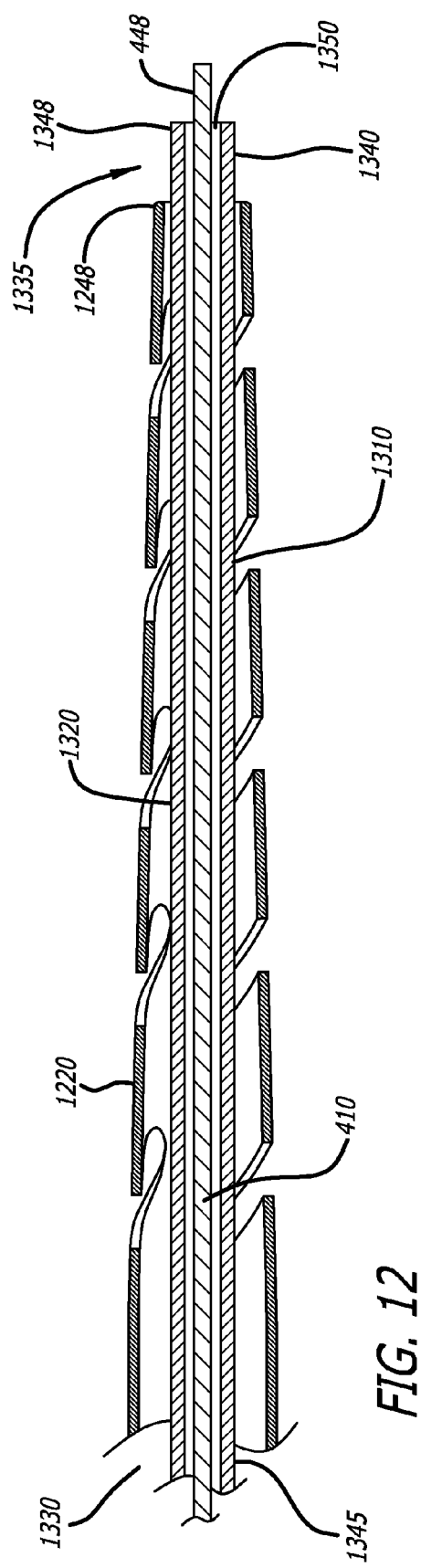
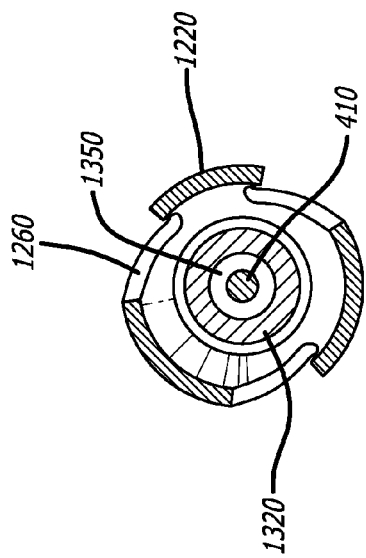
FIG. 12
FIG. 13

DEVICES AND METHODS FOR PERFUSION THERAPY

RELATED APPLICATIONS

The present application is a continuation in part of and claims priority from U.S. patent application Ser. No. 12/702,245 (allowed), entitled "DEVICES AND METHODS FOR PERFUSION THERAPY," by Baxter et al., filed on Feb. 8, 2010, which claims priority from U.S. Provisional Patent Applications Ser. No. 61/150,783, entitled "Devices and Methods for Perfusion Therapy," by Baxter et al., filed on Feb. 8, 2009; and Ser. No. 61/263,790, entitled "Devices and Methods for Perfusion Therapy," by Baxter et al., filed on Nov. 23, 2009; the full disclosures of which are incorporated herein by reference.

BACKGROUND

The present invention is directed to perfusion devices and methods, in particular to devices and methods for cerebral perfusion therapy, including those for use in the treatment of acute ischemic stroke.

All publications, patents, and published patent applications referred to herein are incorporated herein by reference in their entirety.

SUMMARY

Stroke is one of the most devastating medical conditions our society faces. The American Heart Association reports that stroke occurs every 45 seconds, accounting for 1 in 16 deaths, with about 750,000 cases in the United States in 2008. It is the second leading cause of death worldwide and the number one reason for nursing home admissions each year in the United States. It can affect individuals at any age, including the very young.

Stroke occurs when the arteries leading to, or within, the brain become interrupted. Such a blood vessel may become blocked (ischemic stroke) or may rupture (hemorrhagic stroke). Ischemic stroke, caused by blockage of blood flow, is the most common type of stroke. Once the brain is deprived of blood, and thereby the oxygen which it carries, affected brain tissue becomes dysfunctional and ever increasing, potentially irreversible, tissue damage ensues.

Stroke represents a medical emergency and is a potentially reversible process. When large vessels are involved, stroke may be associated with the irreversible destruction of approximately one hundred and twenty million neurons each hour the obstructing lesion ("thrombus") goes untreated. Rapid reperfusion and removal of the thrombus is critically important. The obstructing lesion that interrupts the carotid arterial or cerebral arterial circulation may originate from below the brain, such as in the heart, or form in situ within the arterial circulation itself. Large vessel strokes most frequently involve the territory of the Middle Cerebral artery. Shortly after a thrombus interrupts blood flow to a large artery in the brain, the "Core" area of brain tissue, most severely lacking in blood flow, will begin a process of irreversible cell damage. This area is surrounded by a zone ("the Ischemic Penumbra") that eventually will be irreversibly damaged if blood is not restored within short order. The goal of stroke therapy is to provide blood flow to the "Core" and "Penumbral" areas as rapidly as possible. While there are many types of stroke symptoms, indicative of ischemia to these regions, the most common symptoms are sudden numbness or weakness in the face, arm, and/or leg on one side of the body. Rapid symptom recognition and transport to an appropriate hospital is critical so that treatment to reverse this ischemic process can be attempted.

Prior to 1996, no approved treatment to reverse brain ischemia in acute stroke was available. In 1996 the pharmaceutical compound tissue plasminogen activator (t-PA) received approval by the Food & Drug Administration (FDA) for the treatment of acute ischemic stroke. This drug could, in some cases, stop and reverse stroke by dissolving the obstructing thrombus. The benefit of t-PA, however, is limited in that it has significant clinical benefit in only approximately 12% of patients who receive it as therapy for acute ischemic stroke. Furthermore, in the case of ischemic stroke due to obstruction at the level of the large proximal vessels of the brain, i.e., proximal Middle Cerebral Artery, Basilar, or Internal Carotid Artery less than 10% of patients treated benefit significantly. Current FDA restrictions limit utilization of t-PA to administration within three hours from onset of stroke symptom. Furthermore, numerous other exclusion criteria exist such that less than 5% of patients who experience a stroke in the United States actually receive t-PA yearly. Due to an ever increasing number of people over age 65 (and the expected 2.5-fold increase in atrial fibrillation over the next 50 years) a steady rise in the number of strokes due to large vessel embolic occlusions is expected. As the population ages, therefore, not only is the total number of ischemic stroke per year expected to increase but so is the percentage of strokes amenable to endovascular therapies. This underscores the tremendous opportunity to develop a rapid neuro-protectant device whose function is immediate large vessel arterial reperfusion. As the total cost to society of ischemic stroke for the period of 2005 to 2050 was recently projected to be $2.2 trillion the introduction of new technologies to mitigate stroke impact are of the utmost priority.

New devices designed for mechanical thrombectomy in acute ischemic stroke have been approved for use by FDA. One such device, the "MERCI" device ("Mechanical Embolus Removal in Cerebral Ischemia", manufactured by Concentric Medical, Mountain View, Calif.) is used to extracting and removing thrombus from the brain of acute stroke patients. A second endovascular device, operating on the principle of suction (the Penumbra device), has also received FDA approval for use in patients with acute ischemic stroke.

Although FDA approval of t-PA and certain endovascular devices represents a significant advancement in the field of stroke medicine, the majority of patients experiencing large strokes today still demonstrate poor outcomes. Therefore, there still exists a great need for improved devices and methods for rapid cerebral tissue reperfusion for patients experiencing acute ischemic stroke. The present invention, addresses this and many other needs in this area.

SUMMARY

The present invention relates to treatments, devices, systems, and assemblies, which allow for and/or enable the passage of blood, oxygen, lytic therapy, neuroprotectants and thrombectomy devices, directly through or in the vicinity of an obstructing thrombus.

In an embodiment, the devices and methods of the present invention may be useful in cerebral perfusion therapy, and particularly to treat ischemic stroke.

The present devices and methods provide sufficient blood flow and oxygenation to help minimize neuronal tissue damage thus enhancing clinical recovery of a stroke patient.

In an embodiment, the present devices and methods provide blood and/or oxygen to a target vessel of interest, rapidly reperfusing brain tissue and thereby mitigating the ischemic process and minimizing brain cell death. An important predictor of good outcome in the treatment of such strokes, including treatment with endovascular devices, appears to be time to reperfusion of blood to brain tissue. Extraction of an obstructing thrombus deep within the brain of a stroke patient is a tedious and time consuming process even for highly skilled interventionalists. Numerous endovascular studies demonstrate that endovascular thrombectomy therapy for acute stroke may be a lengthy procedure, with durations often of over one to two hours, during which time brain cells lack critical nutrients essential for viability thereby increasing likelihood of patient morbidity and death. As such, and without intending any limitations, it is believed that the present devices and methods facilitate down-stream blood flow to the brain of patients experiencing acute ischemic stroke for the purpose of enhancing clinical recovery.

In an embodiment, the treatments, and methods, embodying features of the present invention, include the use of a new device and/or system and/or assembly embodying features of the present invention. The present system is referred to as the Neuronal Protection System ("hereafter for purposes of brevity, referred to as "NPS"), including a Neuronal Protection Device ("hereafter for purposes of brevity, referred to as "NPD").

In an embodiment an assembly for perfusion therapy includes a an outer catheter including an elongate member having proximal and distal ends, proximal and distal portions, an inner lumen extending along at least the distal portion, and a plurality of apertures disposed along the distal portion and extending from an outer surface of the elongate member to the inner lumen. The apertures aid in the delivery of any one or more of blood, therapeutic, diagnostic, or other suitable fluids through the outer catheter and/or inner catheter to or to the vicinity of the thrombus site. The distal end of the outer catheter may be tapered in the distal direction. Without intending any limitations, it is believed that the distal taper, in some embodiments, may minimize hemolysis of the blood at the treatment site, as will be further explained below. The tapered distal end may aid in navigating through the thrombus during advancement of the device.

In one embodiment, the assembly further includes an inner catheter including an elongate member having proximal and distal ends, proximal and distal portions, a lumen extending along at least the distal portion. The inner catheter is configured for movable disposal adjacent the apertures of the outer catheter and to movably at least partially obstruct the apertures. In an embodiment, the inner catheter is configured for movable disposal within the inner lumen of the outer catheter and to movably at least partially obstruct the apertures. The elongate member of the inner catheter may be a tubular member or a retractable sheath. The inner catheter may be disposed on the exterior of the outer catheter. The blood or other suitable fluids may be directed from the perfusion pump through the inner lumen of the inner catheter, as when the inner catheter is disposed within the inner lumen of the outer catheter, and through the outer catheter aperture to the desired treatment site. In some embodiments where the inner catheter is disposed on the exterior surface of the outer catheter, blood or other suitable fluids may be pumped through the inner lumen of the outer catheter.

In an embodiment, the assembly further includes a guide catheter having an inner lumen configured to receive the outer catheter therein. The inner catheter, depending on the design may be disposable within the inner lumen of the outer catheter or longitudinally in between the guide catheter and the outer catheter (as when the inner catheter is disposed on the exterior of the outer catheter). The assembly may also include a guidewire disposable in the inner lumen of the inner catheter and/or outer catheter to aid in the advancement of the device within the patient's body.

In an embodiment, a perfusion system includes a outer catheter including an elongate member having proximal and distal ends, proximal and distal portions, an inner lumen extending along at least the distal portion, and a plurality of apertures disposed along the distal portion and extending from an outer surface of the elongate member to the inner lumen. The apertures aid in the delivery of any one or more of blood, therapeutic, diagnostic, or other suitable fluids through the outer catheter and/or inner catheter to or to the vicinity of the thrombus site. The distal end of the outer catheter may be tapered in the distal direction. The system further includes an inner catheter including an elongate member having proximal and distal ends, proximal and distal portions, a lumen extending along at least the distal portion. The inner catheter is configured for movable disposal adjacent the apertures of the outer catheter and to movably at least partially obstruct the apertures. In an embodiment, the inner catheter is configured for movable disposal within the inner lumen of the outer catheter and to movably at least partially obstruct the apertures. The elongate member of the inner catheter may be a tubular member or a retractable sheath. The inner catheter may be disposed on the exterior of the outer catheter. The blood or other suitable fluids may be directed from the perfusion pump through the inner lumen of the inner catheter, as when the inner catheter is disposed within the inner lumen of the outer catheter, and through the outer catheter aperture to the desired treatment site. The system further includes a perfusion pump fluidically connectable to either or both the outer catheter and inner catheter and is configured to actively supply blood to a thrombus site through the outer catheter/inner catheter. In some embodiments where the inner catheter is disposed on the exterior surface of the outer catheter, blood or other suitable fluids may be pumped through the inner lumen of the outer catheter.

In an embodiment, the blood is provided to the perfusion pump by way of a conduit in fluid communication with the patient's own blood supply. In an embodiment, the blood is delivered from the perfusion pump to the patient under pressure. The blood may be cooled prior to being pumped from the perfusion pump to the patient. The blood pumped to the patient may be hyper-oxygenated such that the patient may receive oxygen, normally up to 100% $FIO_2$. In one embodiment, the hyper-oxygenation of the blood supply from the patient may be done by placing the patient on an external mechanical ventilator, thus providing hyper-oxygenated blood to be perfused via the NPS system.

An embodiment of method for perfusion therapy of a patient includes providing a perfusion device including a outer catheter including an elongate member having proximal and distal ends, proximal and distal portions, an inner lumen extending along at least the distal portion, a plurality of apertures disposed along the distal portion and extending from an outer surface of the elongate member to the inner lumen; and an inner catheter including an elongate member having proximal and distal ends, proximal and distal portions, a lumen extending along at least the distal portion, the inner catheter configured for disposal adjacent the apertures of the outer catheter and to movably at least partially obstruct the apertures. In an embodiment, the inner catheter is configured for disposal within the inner lumen of the outer catheter and to movably at least partially obstruct the apertures. The method further includes providing a perfusion pump fluidically connectable to the perfusion device and configured to actively supply blood to a thrombus site through the outer catheter and/or the inner catheter.

The method further includes advancing intracorporeally the outer catheter and the inner catheter through a patient's artery to a treatment site distal to a thrombus site; retracting the inner catheter proximally to expose at least a portion of the apertures; and pumping blood from the perfusion pump through the outer catheter and/or inner catheter to a treatment site distal to the thrombus site.

In an embodiment of a method, the inner catheter is disposed within the inner lumen of the outer catheter prior to advancement within the patient's body. The inner catheter may be moved proximally within the perfusion catheter lumen to at least substantially obstruct the apertures which are within the thrombus area prior to delivering blood and/or therapeutic and/or diagnostic fluids from the pump to the treatment site.

The blood may be cooled prior to being pumped into the patient. Blood may be supplied from the patient's own blood supply to the perfusion pump. This supplied blood may be withdrawn from the patient real time during the performance of the procedure. The blood pumped to the patient may be hyper-oxygenated such that the patient may receive oxygen, normally up to 100% $FIO_2$. In one embodiment, the hyper-oxygenation of the blood supply from the patient may be done by placing the patient on an external mechanical ventilator, thus providing hyper-oxygenated blood to be perfused via the NPS system.

In an embodiment, the method further includes revascularizing the thrombus site. The revascularization may be performed by advancing an endovasulcar thrombectomy device through the outer catheter and/or inner catheter and performing a thrombectomy procedure.

In an embodiment, the outer and/or inner catheter, independently, have variable flexibility along at least a length thereof. The outer and/or inner catheter, in an embodiment, have greater flexibility in the distal direction.

In an embodiment the outer catheter has a distally tapered distal portion including a distal end. The distal end includes a plurality of apertures extending from an outer surface of the outer catheter to an inner lumen of the outer catheter. The apertures, in an embodiment have an oblong shape having a first transverse dimension and second transverse dimension substantially less than the first transverse dimension.

In some embodiments, the apertures are equally distributed along the outer catheter distal end. In an embodiment, the distance between the apertures remains the same. In an embodiment, the first transverse dimension of the apertures shortens in the distal direction as the apertures near the distal tip. In some embodiments, the apertures first dimension as it shortens distally, still remains substantially larger than the second transverse dimension of the same aperture.

In an embodiment, the oblong apertures form a helix. The helix, in an embodiment, has a plane tangent to a centerline of the catheter, forming an angle α therewith, ranging from about 20 to about 85 degrees, from about 30 to about 80 degrees, normally about 40 degrees. In operation, the oblong apertures provide a fluid flow direction of less than about 90 degrees (e.g., acute) as measured from the surface of the catheter distal end thus providing for a more forward fluid flow.

In an embodiment, the neuronal protection device or NPS including the outer catheter, inner catheter, and guidewire, is sufficiently flexible to bend, at its tapered distal portion, to provide an angle up to about 180 degrees, relative to the catheter in the unbent and straightened configuration. This configuration allows the NPS, in operation, to navigate the intracranial portions of the internal carotid artery which have a 180 degree bend. In an embodiment, the tapered distal portion configured to provide such a bend angle, has a length sufficiently long to navigate the cavernous section of the internal carotid artery. In an embodiment, the distal portion is configured to bend back on itself (e.g., about 180 degrees) over a distance of at least or about 10 mm. In an embodiment, the portion of the tapered distal portion configured to provide such a bend, is the distal end. In an embodiment, the distal end, of the device, normally the entire distal end, is configured to provide a bend angle of at least or about 180 over a distance of at least or about 10 mm. In an embodiment, and in operation, the NPS, in the bent configuration, at its distal end, may have a bend radius of at least or about 10 mm. In an embodiment, and in operation, the outer catheter, in the bent configuration, at its distal end, may have a bend radius of at least or about 10 mm.

In some embodiments, in operation, any one or more of the following may be practiced according to the methods embodying features of the present invention: perfusion of blood or other fluids (e.g., thrombolytic agents) through either the outer catheter or the inner catheter alone; perfusion of blood, TPA, or other fluids simultaneously through both the inner and outer catheters; or perfusion of blood through the inner catheter with the inner catheter distal tip positioned distal to the clot while simultaneously infusing fluids such as tissue plasminogen activator ("TPA) or other thrombolytic agent/s through the outer catheter with its distal tip positioned substantially or entirely in the clot.

BRIEF DESCRIPTION OF THE DRAWINGS

FIG. 2 is an illustration of a neuronal protection device embodying features of the present invention and including an outer catheter and inner catheter with a guidewire disposed therein.

FIGS. 2A and 2B are cross sectional views of the device of FIG. 2 taken along cross-sections AA and BB, respectively.

FIG. 3 is an illustration, partially cut away, of the neuronal protection device of FIG. 2.

FIGS. 3A and 3B are exploded views of portions of the proximal and distal portions of the device of FIG. 2, respectively.

FIG. 9 is a graphical representation of the data presented in TABLE II.

FIG. 10 is an illustration of an alternate embodiment of a neuronal protection device embodying features of the present invention and including a distally tapered outer catheter and an inner catheter with a guidewire disposed therein.

FIG. 11B is an enlarged view of an alternate embodiment of the distal portion of the neuronal protection device of FIG. 10.

FIGS. 11C and 11D are enlarged views of the distal portion of the outer catheter of FIG. 11A.

FIG. 11E is a partial enlarged view of the distal portion of the outer catheter of FIG. 11A.

FIG. 11F is a cross sectional view of the outer catheter distal end of FIG. 11D taken along lines 11F-11F.

FIGS. 12 and 13 are cross sectional views of the device of FIG. 11A taken along cross-sections 12-12 and 13-13, respectively.

The drawings illustrate embodiments of the invention and are not limiting. For clarity and ease of illustration, the drawings are not made to scale and, in some instances, various aspects may be shown exaggerated or enlarged to facilitate an understanding of particular embodiments.

DESCRIPTION

Figure 1:
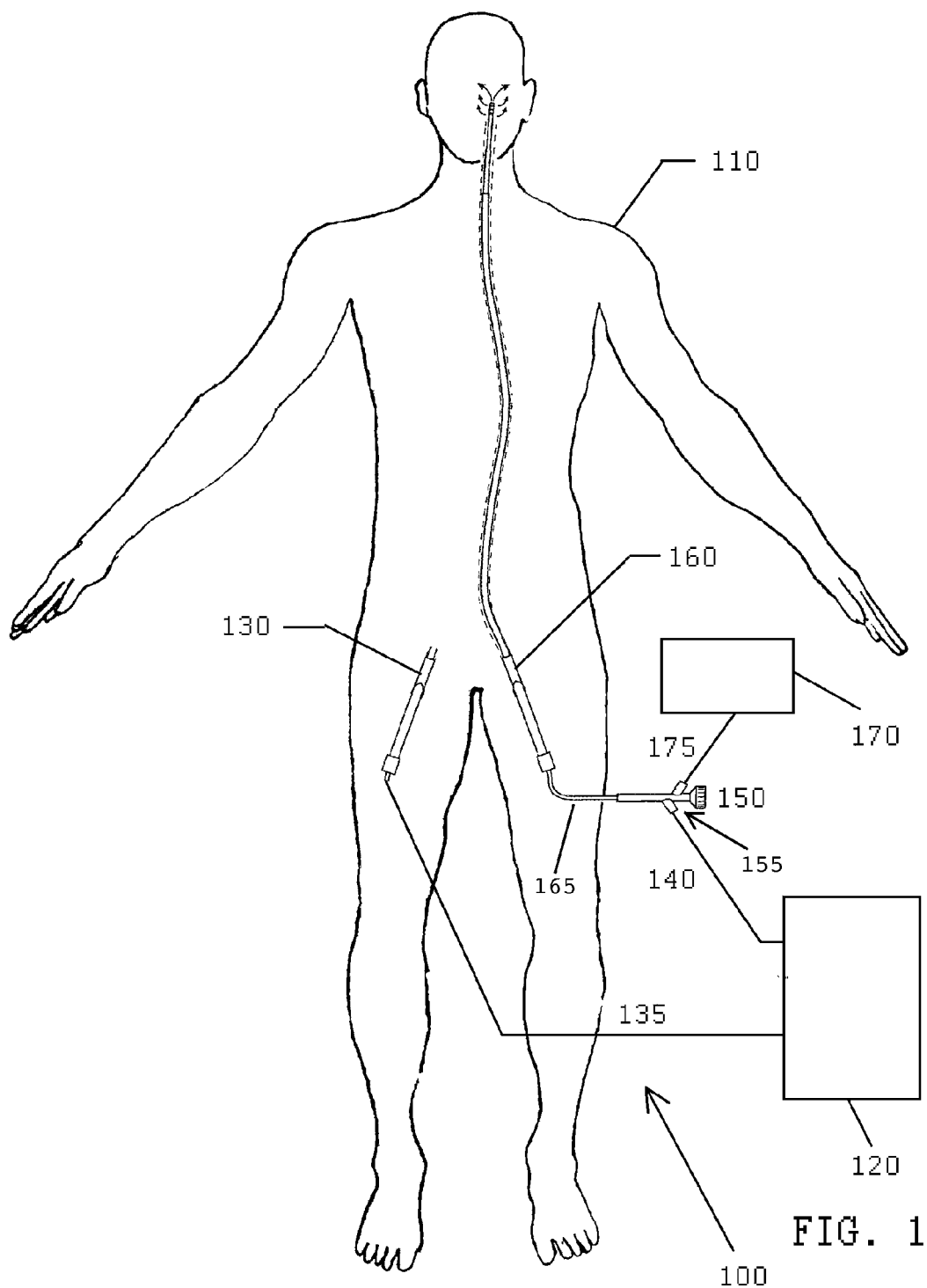
FIG. 1 is an illustration of a neuronal protection system embodying features of the present invention and as in use with a patient.

Referring to FIG. 1, an assembly 100 embodying features of the present invention is shown as set up for treating a patient 110. As shown, the assembly 100 includes a perfusion pump 120 in fluidic communication with an output femoral sheath 130 and connector 135. The Connector 135 enables movement of blood from the femoral arterial sheath which is insertable into one of the femoral arteries of the patient by being attached to the perfusion pump.

A connector 140 fluidically connects the perfusion pump 120 through port 150 of a hemostatic valve 155 to an input femoral artery sheath, 165 through connector 165. A source 170 of therapeutic and/or diagnostic fluid is also in fluid communication with the perfusion device through port 175 of the valve 155.

Now referring to FIGS. 2, 2A, and 2B, a neuronal protection device 200, embodying features of the present invention is shown, including an outer catheter 210 including an elongate member such as a tubular member 220 having distal and proximal ends, 230 and 235, distal and proximal portions, 240 and 245, and distal tip 248. An inner lumen 250 extends longitudinally at least along the distal portion of the outer catheter. The distal end includes one or more apertures 260 extending from an outer surface 265 of the outer catheter to the outer catheter inner lumen 250. The apertures aid in the delivery of any one or more of blood, therapeutic, diagnostic, or other suitable fluids through the outer catheter and/or an inner catheter to or the vicinity of the thrombus site.

In an embodiment, the distal portion 230 of the outer catheter is distally tapered. Without intending any limitations, it is believed that the distal taper, in some embodiments, may minimize hydrolysis of blood during the treatment, as will be further explained below. The tapered distal end also aids in navigating through the thrombus during advancement of the device 200. In an embodiment, the tapered distal end assists with minimizing the hemolysis of the blood at the treatment site.

An inner catheter 310, as shown, is disposed inside at least a portion of the inner lumen 250 of the outer catheter 210. The inner catheter 310 includes an elongate member such as a tubular member 320 having distal and proximal ends, 340 and 345, distal and proximal portions, 335 and 330, and a distal tip 348. An inner lumen 350 extends longitudinally at least along the distal portion of the inner catheter. As shown, the distal end of the inner catheter extends into the distal portion of the outer catheter and extends distally beyond the outer catheter distal end. The blood or other suitable fluids may be directed from the perfusion pump through the inner lumen of the inner catheter, as when the inner catheter is disposed within the inner lumen of the outer catheter, and through the outer catheter apertures to the desired treatment site, or through inner catheter's distal tip 348.

A guide wire 410, as shown, is disposed in the inner lumen 350 of the inner catheter 310, with a distal tip 448 of the guide wire 410 extending distal of the distal tip 248 of the outer catheter 210 and the distal tip 348 of the inner catheter.

Now referring to FIGS. 3, 3A and 3B, the device 200 is shown disposed in an inner lumen 550 of a guide catheter 510, and extending distally from a distal tip 548 of the guide catheter.

The outer catheter and inner catheter may be designed and constructed to meet the necessary requirements of the anatomy. In an embodiment, some of the components, construct, size, and material of the outer catheter and inner catheter may be similar to those used in delivering the MERCI device into the brain, the details of which are incorporated herein by reference. In some embodiments, the outer catheter may normally have an internal diameter ranging from about 1.0 mm to about 1.5 mm; with the outer catheter distal tip, when tapered, having a length ranging from about 15 mm to 30 mm.

The aperture size for the outer catheter typically ranges from about 0.1 mm to about 0.5 mm. The typical catheter lengths for the outer catheter are in the 135 cm range and for the inner catheter, the 150 cm range.

In embodiments of methods of treatment embodying features of the present invention, one or more of the following steps may be utilized, as deemed necessary by the practitioner:

Typically, a patient exhibiting a stroke will be evaluated emergently by a medical stroke expert. A computerized tomography (CT) scan of the brain is performed to confirm that the stroke is ischemic, not hemorrhagic, and to assist in localization of the obstructing thrombus. The stroke specialist will determine if the thrombus is located within an artery supplying the brain and whether the thrombus is amenable to endovascular extraction by an interventionalist physician (as for example by using the MERCI or Penumbra device). If the patient is deemed an appropriate candidate for the procedure, the patient may undergo a standard intubation procedure (i.e., placed on a ventilator) for airway protection and to facilitate hyper-oxygenation. The patient may receive oxygen at an $FIO_2$ of up to 100%. The patient is then brought to the endovascular suite. Arterial access is gained by placement of a short femoral arterial sheath 130 (FIG. 1). A sheath that is large enough to allow blood withdrawal around the guide catheter/outer catheter may be selected or the operator may choose to place a second sheath 160 in the contralateral femoral artery that is for the purposes of blood delivery to the perfusion pump (FIG. 1). The blood is delivered to the perfusion pump via Connector 135.

In exemplary embodiment of a method embodying features of the present invention, thereafter, using standard angiographic technique, a guide catheter 510 will be inserted by way of the femoral sheath 160 and advanced through the aorta into one of the larger cervical arteries (the Carotid or Vertebral arteries) that supplies the occluded vessel at the base of the brain. A liquid "contrast" material is pumped through the guide catheter (an angiogram), to determine exactly where the occluding thrombus is located.

It should be appreciated by those skilled in the art, that the methods embodying features of the present invention, as described herein, may include any one or more of such steps not necessarily being described. Outside of the patient's body, the outer catheter 210 and inner catheter 310 are prepared for delivery by placing a rotating hemostatic valve (RHV) at the proximal end for continuous infusion of heparinized saline. The guide wire 410 is placed in the lumen 350 of the inner catheter 310 and this inner catheter/guide wire unit is then advanced through the inner lumen 250 of the outer catheter 210 until the tip of the inner catheter/guide wire extends distal to the distal tip 248 of the outer catheter.

Figure 4:
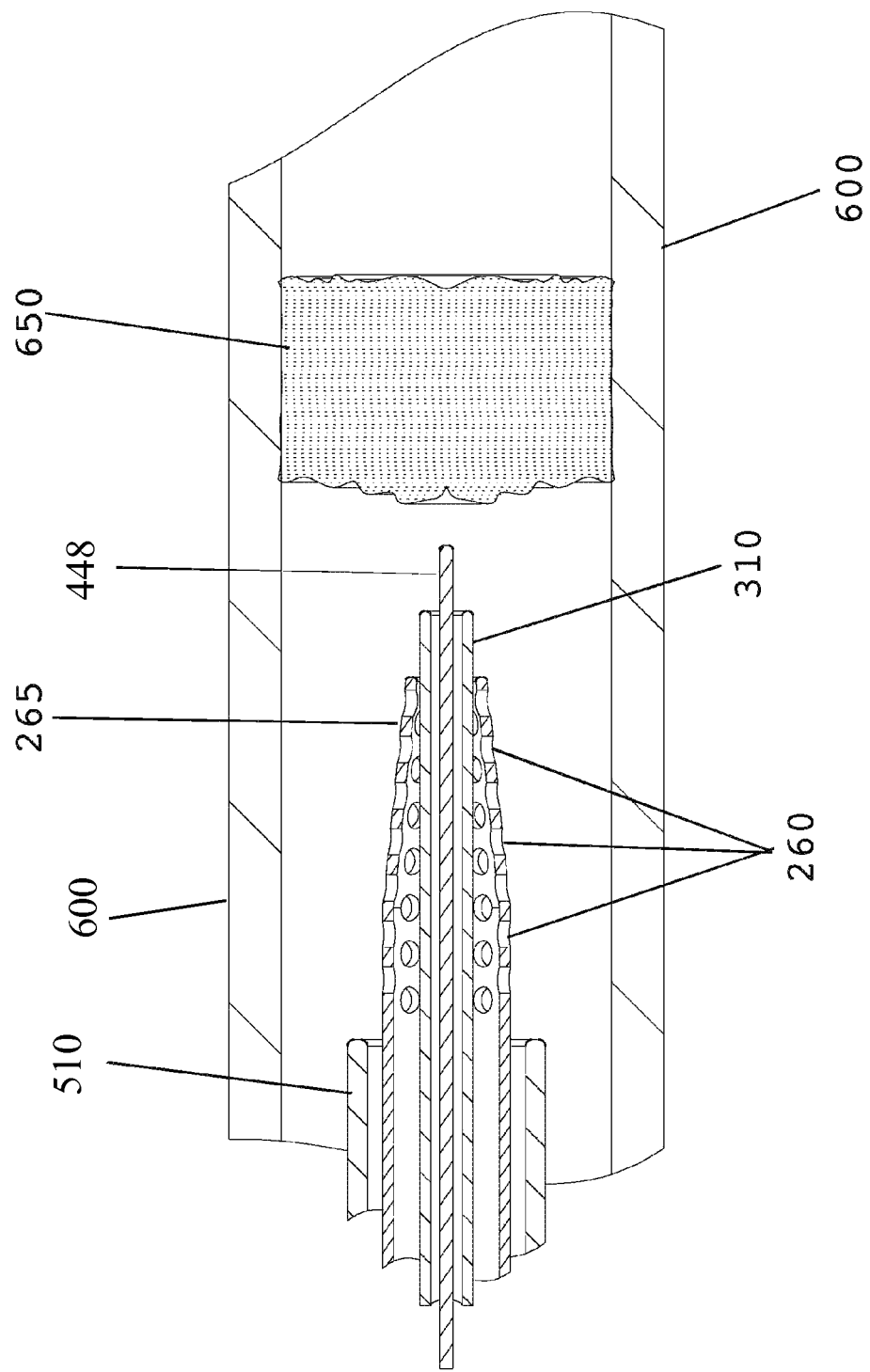
FIG. 4 is an illustration of the perfusion device of FIG. 2 disposed in a patient's lumen proximal to a thrombus site.
Figure 5:
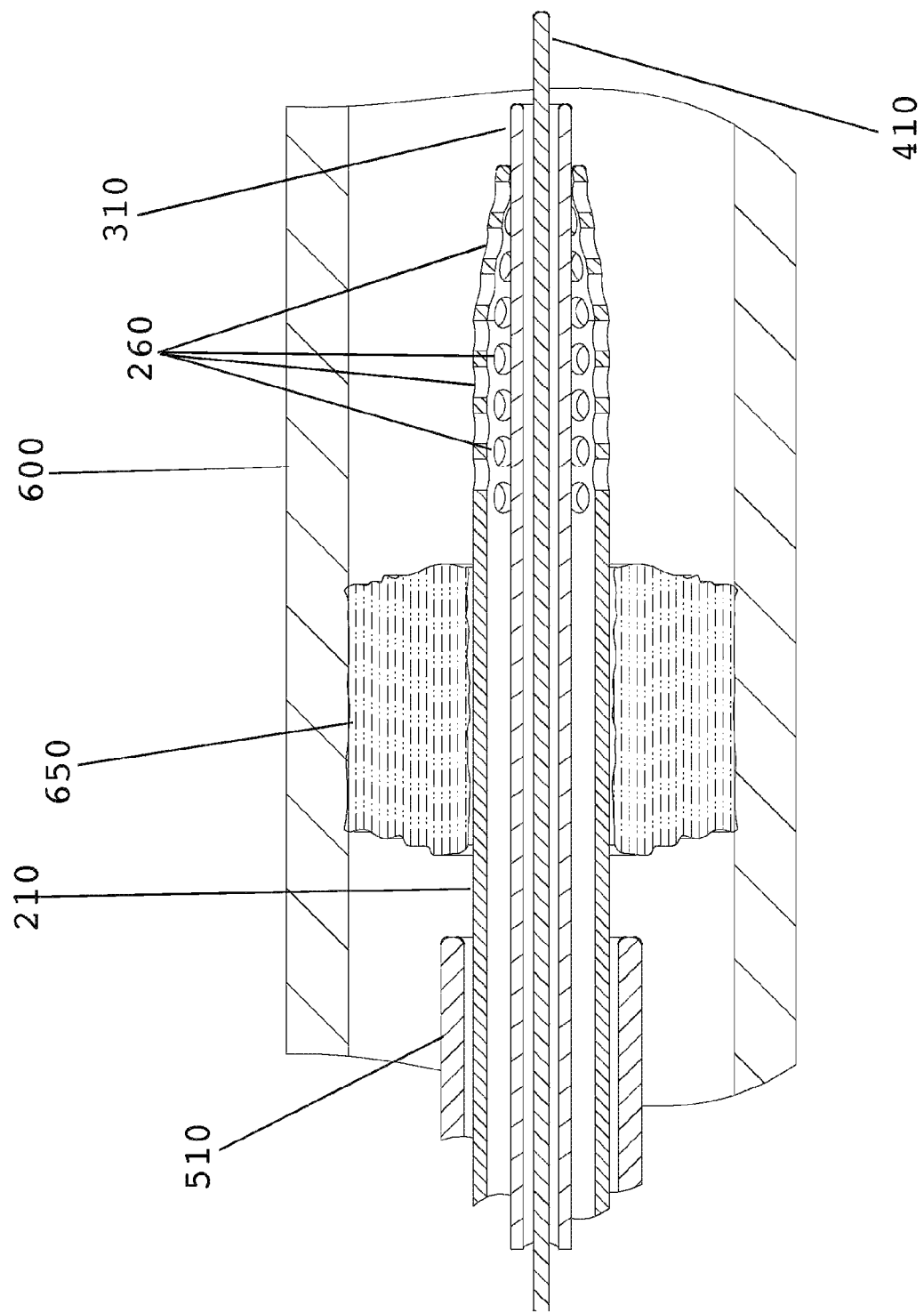
FIG. 5 is an illustration of the perfusion device of FIG. 4 disposed in a patient's lumen with the perfusion device distal portion disposed distal to a thrombus site.
Figure 6:
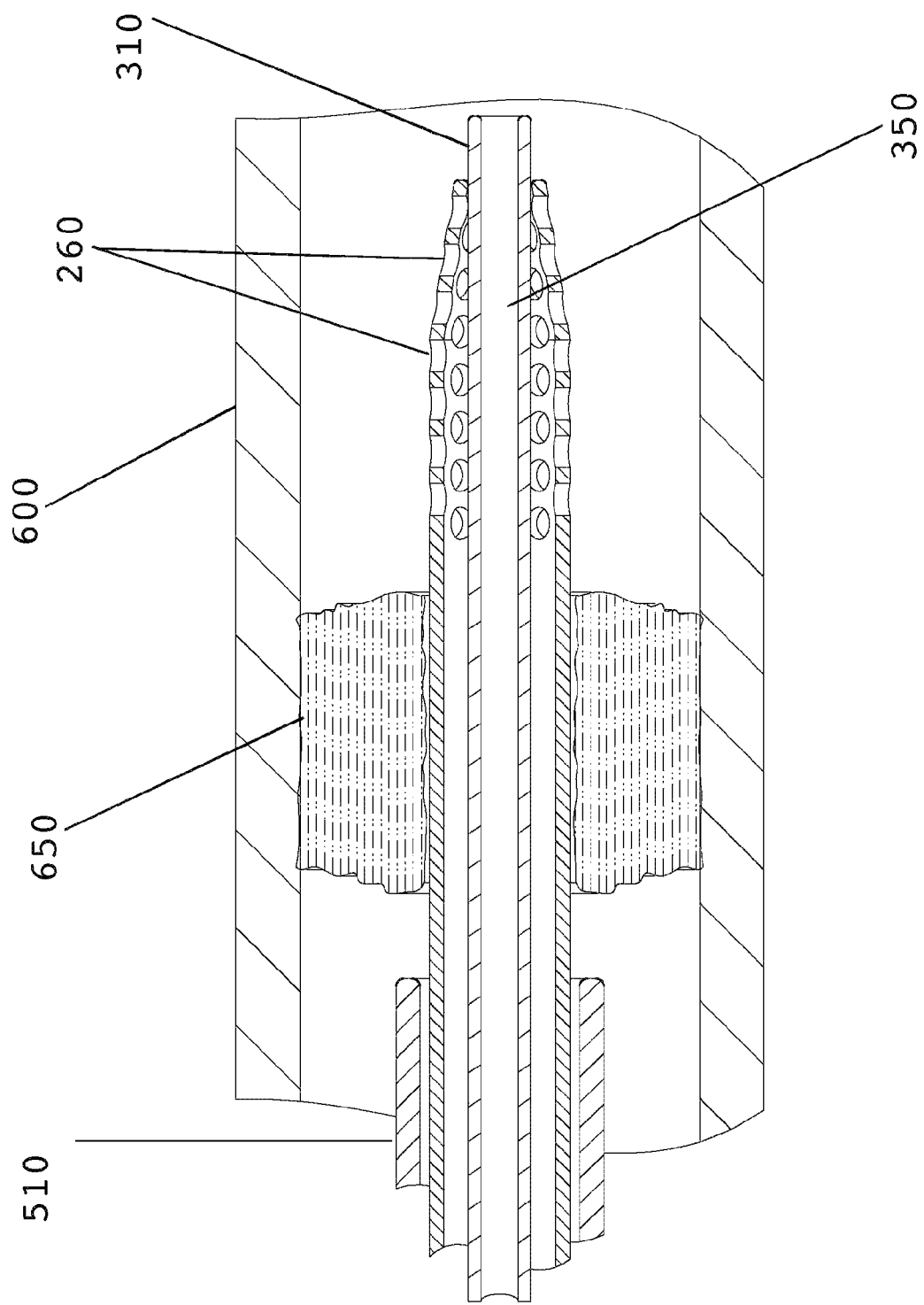
FIG. 6 is an illustration of the perfusion device of FIG. 5 with the guidewire removed.

In some embodiments, the inner catheter may serve as a platform for delivery of thrombectomy devices/lytics and/or therapeutic and/or diagnostic fluids, if desired. In an embodiment, this entire catheter combination (outer catheter/inner catheter/guide wire) is then introduced through the guide catheter 510 and advanced to the target vessel 600 using standard microcatheter techniques, as partially shown in FIG. 4. The tips of outer catheter/inner catheter/guidewire are advanced distal to the obstructing thrombus 650, as shown in FIG. 5. The guidewire is thereafter removed (See FIG. 6). It may be desirable to confirm that the outer catheter tip is located distal to the thrombus by injecting a small amount of contrast. In an embodiment in the case that only a segment of the entire length of perfusion apertures are exposed distal to the thrombus, the inner catheter may be used to deliver blood flow. The inner catheter tip is withdrawn proximally to expose the perfusion apertures.

Figure 7:
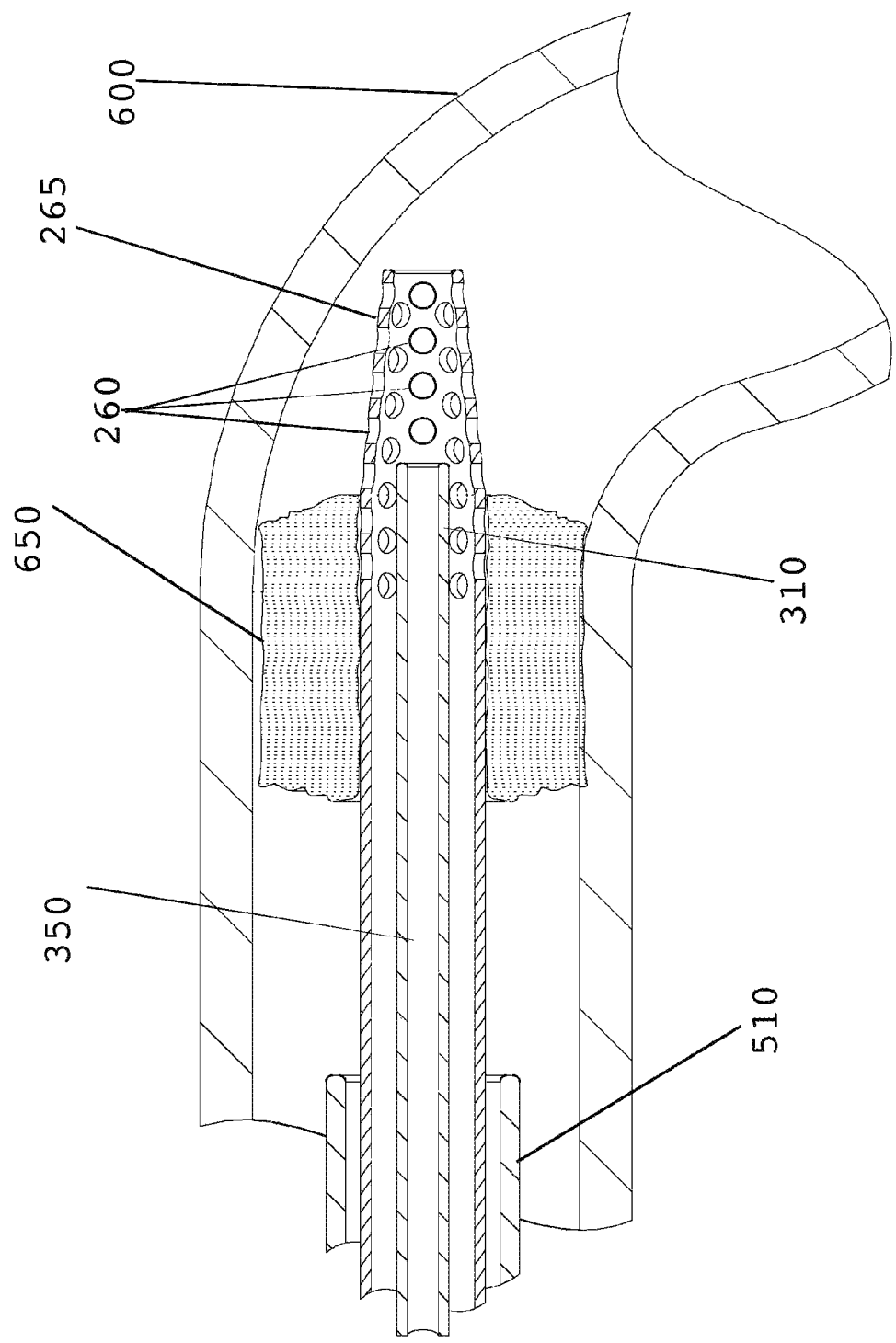
FIG. 7 is an illustration of the perfusion device of FIG. 5 with the only a portion of perfusion apertures disposed distal to the thrombus.
Figure 8:
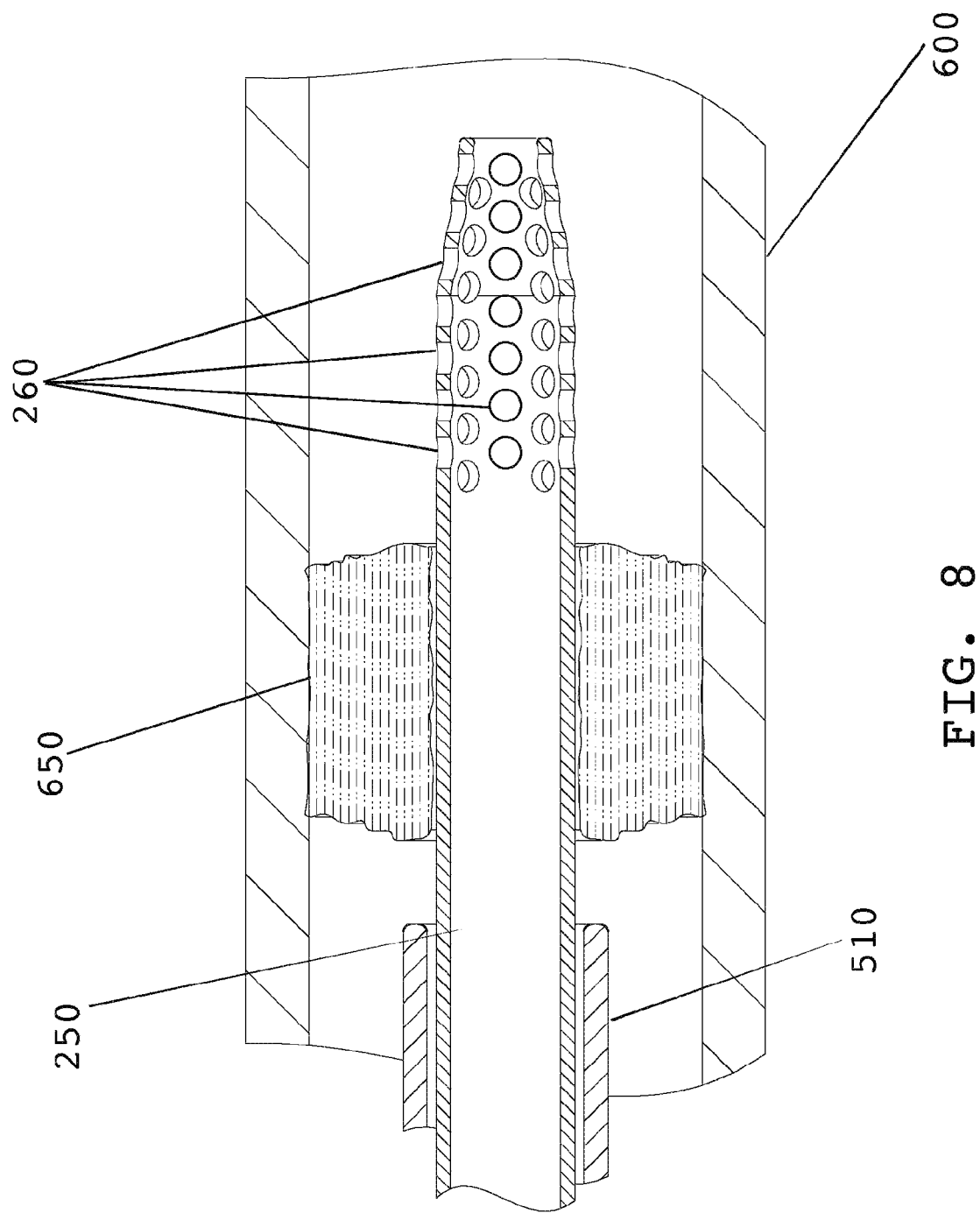
FIG. 8 is an illustration of the perfusion device of FIG. 2 with the inner catheter removed from a guide catheter.

In an embodiment, as shown in FIG. 7, the inner catheter tip is withdrawn proximally to expose the maximum number of perfusion apertures that are distal to the thrombus while continuing to cover (e.g., disposed adjacent the apertures so as to minimize flow of blood or other therapeutic/diagnostic fluids pumped or delivered through the outer catheter/inner catheter) the perfusion apertures that are at the level of or proximal to the thrombus. The inner catheter is then attached to the perfusion pump and perfusion is initiated with blood flow being directed to the apertures distal to the thrombus. In the case that the landing area in the artery allows exposure of the entire length of the aperture section, then the inner catheter may be removed and the outer catheter is attached to the perfusion pump and perfusion is initiated (See FIG. 8).

In an embodiment, thrombolytic agents may be used to enhance the treatment. In an embodiment, a sufficiently effective small quantity of contrast is injected through the device to demonstrate the distal end of the thrombus. Standard angiographic run is performed through the guide catheter to outline the proximal end of the thrombus. The inner catheter is withdrawn to expose the maximum number of perfusion apertures of the outer catheter. The thrombolytic agent is thereafter introduced into the desired area.

In an embodiment, it may be desirable to perform intra-arterial mechanical thrombectomy. In an embodiment, a sufficiently effective small quantity of contrast is injected to confirm that the NPS catheter tip is distal to the thrombus. A thrombectomy device is introduced through the inner catheter/PC combination and thrombectomy is performed according to device procedural guidelines, all of which by example are incorporated herein by reference (Mechanical Embolus Removal in Cerebral Ischemia", manufactured by Concentric Medical, Mountain View, Calif.).

In an embodiment, the thrombus may have a length ranging from about 1 cm to about 18 cm. The artery "Landing Area" beyond the thrombus generally has a vessel diameter range from about 1.5 mm to about 2.5 mm with the thrombosed artery generally ranging from about 2.5 mm to about 4.0 mm in diameter.

The perfusion pump is similar to those used in pumping blood through the cardiac arteries during heart surgery, the details of which are incorporated herein by reference, with the additional inventive features described herein and further below.

In an embodiment, the perfusion pump incorporates a volumetric displacement pump configured to provide pressure controlled delivery of oxygenated blood at flow rates necessary to support the affected region of the brain distal to an arterial occlusion through a micro-catheter at pressures above 1,000 mm Hg. In an embodiment, the pump mechanism is a dual chamber piston pump; although, if non-continuous flow is acceptable a single chamber system could be adapted. In an embodiment, additional high pressure single-chamber pump(s) that contribute neuroprotective agent(s) to the perfusate may be used. The system may also incorporate a perfusate temperature control system to either maintain normothermia or hypothermia to reduce metabolism and aid in recovery and the mitigation of reperfusion injury. In an embodiment, the hardware of the integrated system interfaces with a sterile disposable delivery set that contains the conduits for carrying arterialized blood from the patient to the neuro-perfusion system and then to the micro catheter.

Also contained within the sterile disposable delivery set are pump cassettes that interface with the piston pumps. The sterile disposable are pump may include cassettes that interface with the piston pumps. A heat transfer device may be sued to serve as the medium for transferring heat energy to and from the perfusate. Safety devices and components including emboli detectors may further be employed. The maximum pump pressure as compared to cardiac pumps is modified to allow for pumping of blood up the outer catheter so that blood may be delivered distal to the thrombus perfusing the ischemic brain tissue at an appropriate flow rate range of 50 to 150 ml/min.

By placing the patient on an external mechanical ventilator the patient may receive oxygen at up to 100% $FIO_2$ thus providing hyper-oxygenated blood to be perfused via the NPS system. As seen in FIG. 1, the blood moves out of the patient's body (through the sheath in the patient's femoral artery or from a second access site), through connector 135 to the perfusion pump. The pump then delivers the blood to the outer catheter via connector 140. In an embodiment, the perfusion pump may also cool the blood, a technique called "hypothermia." Without intending any limitations, it is believed that the cooling of the patient's blood may have a "neuro-protective effect" on the brain that delays the destruction of brain cells until blood flow is restored. The perfusion pump may also be used to add other suitable drugs to the blood, such as, but not limited to chemical "neuro-protectants" that may be of benefit when delivered directly to the stroke brain tissue.

In an embodiment, the inner catheter takes on the form of a retractable sheath disposable within the inner lumen of the outer catheter. In this embodiment, a distal end of the inner catheter may be proximally retractable by suitable means such as a wire connected to the inner catheter distal end, with a proximal end of the wire extending proximally from the proximal end of the outer catheter. In this configuration, the apertures are covered (or fluid flow may be at least partially obstructed) by the sheath and may be exposed, as desired, by retracting the sheath proximally by way of the wire. Alternatively, the sheath may be disposable over the exterior surface of the outer catheter and is retractable by suitable means such as wire. In another embodiment, the inner catheter may be a tubular member disposable over the exterior surface of the outer catheter. Retraction of the inner catheter in the proximal direction exposes the apertures for fluid delivery.

Below, are exemplary applications of the NPS devices and methods embodying features of the present invention. In first exemplary application, embodying features of the present invention, as discussed above, the NPS will be utilized as a reperfusion platform for carrying out an endovascular acute stroke procedure targeted at medium to large vessel occlusions. NPS reperfusion will be implemented at the start of the procedure to achieve instantaneous reperfusion to facilitate and restore normal oxygen levels in the ischemic penumbra thereby minimizing permanent neuronal damage. Once the initial NPS tissue rescue reperfusion step is complete, a revascularization method can be employed to obtain permanent vessel patency. If such revascularization involves utilization of a MERCI, Penumbra, or other similar devices, the NPS platform will allow that device to be inserted within and through the NPS for attempting the thrombectomy portion of the procedure. Thrombus extraction may then be performed as needed. As thrombectomy procedures often require use of multiple types of devices over several hours, continuous or cyclical NPS tissue rescue reperfusion may be utilized adjunctively during the endovascular procedure. As it is recognized that acute ischemic stroke is heterogeneous (carotid versus intracranial; embolic versus medium to large vessel in situ atherosclerotic disease), this first exemplary application of the NPS provides a general platform for neuronal rescue from which a number of therapies can be performed (including but not limited to intravenous/intra-arterial pharmacological thrombolysis, mechanical thrombus removal, stenting, or other forms of neuroprotection).

Yet it is recognized that a significant percentage of clinically devastating strokes involve vessels which due to size or location are not amenable to mechanical clot extraction (for example, lacunar stroke, distal branch MCA thrombus, etc.). In a second exemplary application, embodying features of the present invention, includes utilization of the NPS to provide neuronal protection via augmentation of collateral arterial flow (increased tissue oxygenation and egress of cytotoxic compounds), and/or localized delivery of hypothermia or other neuroprotectant directly to the ischemic vascular bed. It should be recognized that this second exemplary application may be used in conjunction with other intravenous thrombolytic or neuroprotectant therapies.

It is recognized that many acute stroke patients initially are directed to hospitals where advanced stroke care is not available. A third exemplary application embodying features of the present invention, the NPS involves its use as a generalized neuronal protection bridging device in which NPS therapy is initiated at the first responder hospital and maintained during transport to a hospital which offers the full complement of acute stroke treatment options.

In order to assess the feasibility of the devices and methods of the present invention, certain experiments were performed and data collected. This data is presented by way of example and not limitation. By way of explanation and not limitation, it is believed, that that blood flow rates in the range of about 50-150 ml/min through the catheters of the present invention into the large arteries of the brain are desired to normalize oxygen levels in the tissue. Using two catheters (a small Concentric 18 L and the larger DAC), it was demonstrated, as shown in Table I below, that the present method was successful in obtaining flow rates with saline above 200 ml/min using the larger DAC catheter. This data demonstrate the feasibility of achieving the goals of the NPS. Data were generated utilizing a perfusion pump with the characteristics described above.

TABLE I

Initial Saline Pressure-Flow Test Results Using Two Concentric. Micro-catheters

|  | Pressure (mmHG) | Flow (ml/min) |
| --- | --- | --- |
| Catheter 1 - MC-18L (ID = 0.019 in) | 500 | 4 |
|  | 1100 | 15 |
|  | 1400 | 18 |
| Catheter 2 - DAC (4.3F OD-3.3F ID ID = 0.044 in) | 500 | 88 |
|  | 1100 | 165 |
|  | 1400 | 265 |

When a similar feasibility study was performed using whole human blood similar results were obtained despite the introduction of increased viscosity. As demonstrated in Table II, a physiological relevant human blood flow rate of above 100 ml/min through a Concentric DAC microcatheter could be maintained without significantly increasing pump pressure. Furthermore, when hemolysis of whole human blood was analyzed by measuring free Hemoglobin levels during recurrent circulation though the NPS (as performed to generate the results presented FIG. 9), no significant erythrocyte hemolysis was noted. The human blood pressure-flow and hemolysis data presented in TABLES I and II were generated utilized a pump with the characteristics described above.

TABLE II

Pressure-Flow Test Results Using Concentric DAC Micro-catheter Pressure Drop Data with Blood

| Flow Rate (ml/min) | Sys Pressure (mmHG) | Temperature (° C.) |
| --- | --- | --- |
| 0 | 78 | 36 |
| 25 | 287 | 36 |
| 50 | 482 | 37 |
| 100 | 1031 | 37 |
| 120 | 1135 | 37 |

FIG. 9 indicates that at the physiologically relevant blood flow rates anticipated to be generated by the NPS significant hemolysis does not occur and oxygen carrying capacity is not compromised.

Now referring to FIG. 10, an alternate embodiment of the neuronal protection device 1200 is shown, embodying features of the present invention, and including an outer catheter 1210 including an elongate member such as a tubular member 1220 having a proximal portion 1245 with a proximal end 1235, a distally tapered distal portion 1240 with a distally tapered end 1230 terminating in a distal tip 1248.

In an embodiment, the distal portion 1240 is configured, such that in operation, it is juxtaposed with the distal intracranial internal carotid artery upon full placement of the outer catheter within the brain. In an embodiment, the tapered distal portion 1240 aids in navigating through the thrombus during advancement of the device 1200. In an embodiment, and without intending any limitations, it is believed the tapered distal portion assists with minimizing the hemolysis of the blood at the treatment site. The distal tapering of the outer catheter and the relatively larger proximal bore design is further believed to minimize resistance along length of the outer catheter minimizing undesirable pressure drops during the operation of the device.

Figure 11A:
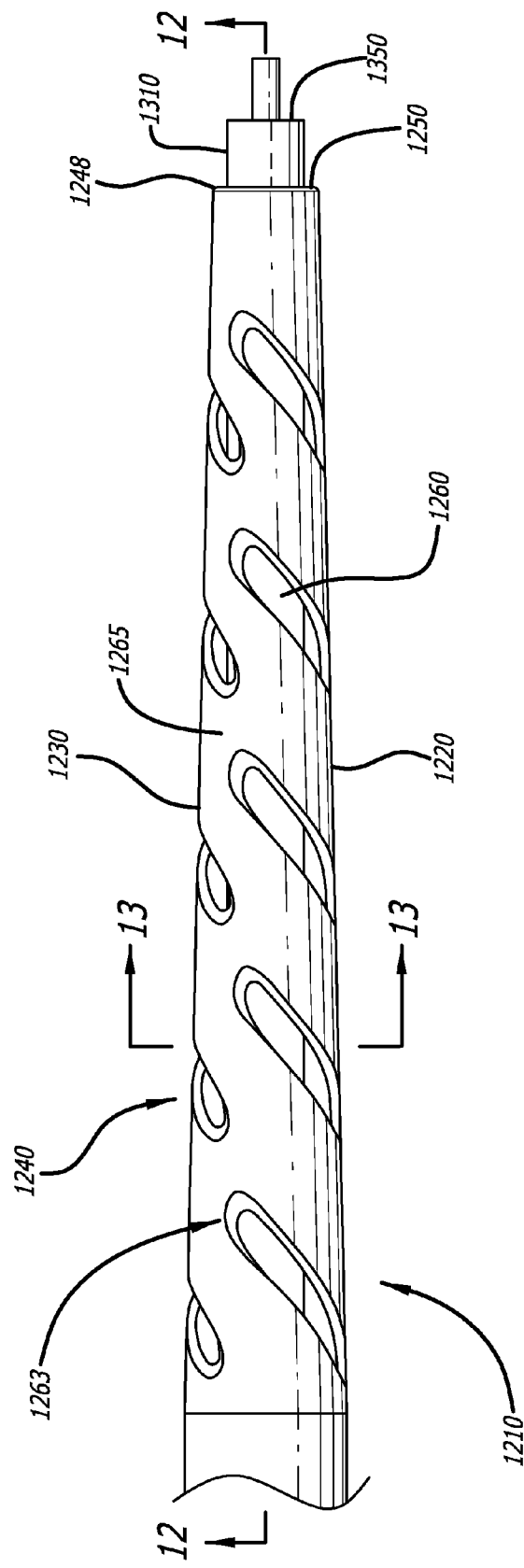
FIG. 11A is an enlarged view of the distal portion of the neuronal protection device of FIG. 10.

The tapered distal end 1230 may have a longitudinal dimension which is the same as that of the tapered distal portion 1240 (see FIG. 10, 11A) or shorter as shown in FIG. 11B.

The outer catheter distal end 1230, as further shown in FIGS. 11A and 11B, 12, and 13, includes one or more apertures 1260 extending from an outer surface 1265 of the outer catheter to an outer catheter inner lumen 1250. The apertures aid in the delivery of any one or more of fluids such as blood, therapeutic, diagnostic, or other suitable fluids through the outer catheter to or to the vicinity of the thrombus site.

In an embodiment, and as shown in FIG. 11B, the outer catheter 1210' has a tapered distal portion 1240' including a distal end 1230'. As shown, the distal end 1230', including apertures 1260', has a longitudinal dimension which is less than the longitudinal dimension of the tapered distal portion 1240'.

Figure 14:
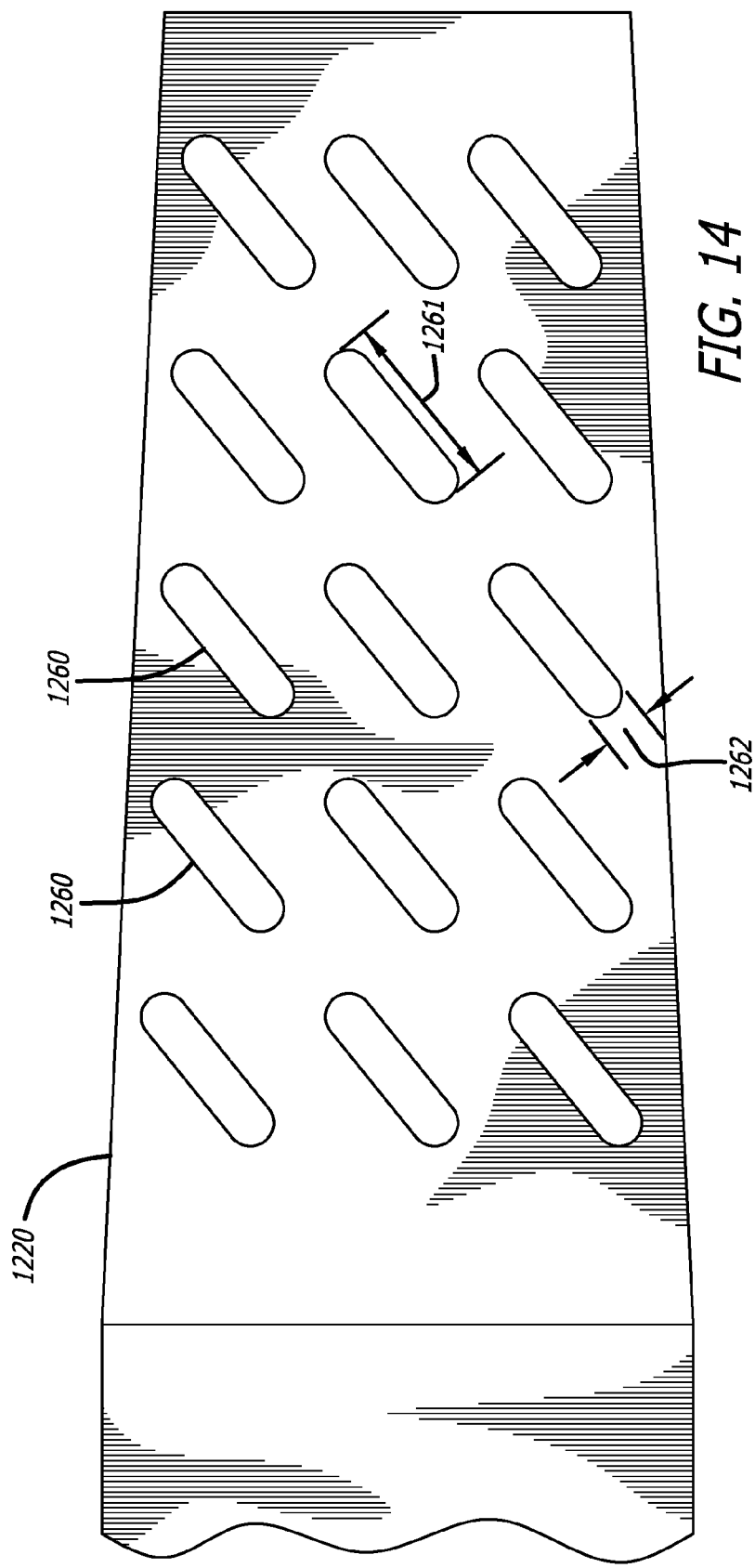
FIG. 14 is a cut away view of the outer catheter distal portion in a flattened configuration showing the elongated apertures, according to an embodiment.

Now referring to FIG. 14, the apertures 1260 are shown with the outer catheter tubular member 1220 in a flat rolled out configuration. The apertures 1260 have a first and a second transverse dimension, 1261 and 1262, respectively. An aperture may have the same or different first and second transverse dimensions from those of a neighboring aperture. The first and second transverse dimensions, may, independently, range from about 0.1 mm to about 0.5 mm.

In an embodiment, the first and second transverse dimensions are substantially equal. In an embodiment, the apertures have an oblong transverse shape with the first transverse dimension in a first direction being substantially greater than the second transverse dimension in a second direction perpendicular to the first direction.

In some embodiments, the distance between the apertures remains the same. In an embodiment, the apertures are equally distributed along the outer catheter distal end. In an embodiment, the first transverse dimension of the apertures shortens in the distal direction as the apertures near the distal tip. In some embodiments, the apertures first dimension as it shortens distally, still remains substantially larger than the second transverse dimension of the same aperture.

In an embodiment, and as shown in FIGS. 11A and 11B, apertures 1260, extend from the outer surface 1265 to the inner lumen 1250 of the outer catheter 1260, forming a helix 1263.

In an embodiment, and as shown in FIGS. 11C, 11D, 11E, and 11F, the helix 1263 has a plane tangent to a centerline of the catheter, forming an angle α therewith, ranging from about 20 to about 85 degrees, from about 30 to about 80 degrees, normally about 40 degrees.

In an embodiment, when the apertures' first and second dimensions are substantially similar, fluid flow from the apertures forms a perpendicular angle with the centerline axis of the shaft or the surface of the tip.

In an embodiment, the oblong (e.g., apertures with first transverse dimension being larger than the second transverse dimension) apertures provide a fluid (e.g., blood, therapeutic agents, diagnostic fluid and the like) flow direction of less than about 90 degrees (e.g., acute angle) as measured from the surface of the catheter distal end.

In an embodiment, the acute angle of the fluid flow from the oblong apertures provides for a less turbulent flow (as compared to that from an aperture having substantially similar transverse dimensions) which, is more in line with the axis of the catheter shaft thus facilitating forward fluid flow.

In an embodiment, the sum of the areas of all the apertures is equal to or greater than the cross sectional area of the outer catheter inner diameter taken at the largest outer catheter inner diameter (e.g., proximal to the proximal end of the tapered distal end).

The distal portion including the distal end, which includes the apertures, and the proximal portion may be formed as an integral part of the outer tubular member 1220, as for example formed during an extrusion process. In an alternative, the distal and proximal portions of the outer catheter tubular member may be separately formed and thereafter joined to one another by any one or more suitable means, including but not limited to: welds, adhesives, sleeves, etc., In an embodiment, the distal end of the proximal portion and the proximal end of the distal portion may form any number of joints, for example butt jointor lap joint (where either of the two ends may be fitted into the other). By way of example, when a welding process is used, the process may be a reflow type of process, where the distal portion and the extruded shaft are formed of the same material and placed over a mandrel and butt-welded to one another using radio frequency energy or hot air to soften the two material. By way of example, a draw-dawn operation through a tapered die may be utilized to achieve the desired taper. The apertures may be laser cut into the distal end or molded in.

Now referring back to FIGS. 10 and 11, 12, and 13, an inner catheter 1310, as shown, is disposed inside at least a portion of the inner lumen 1250 of the outer catheter 1210. The inner catheter 1310 includes an elongate member such as a tubular member 1320 having distal and proximal ends, 1340 and 1345, distal and proximal portions, 1335 and 1330, and a distal tip 1348. An inner lumen 1350 extends longitudinally along at least the distal portion of the inner catheter. As shown in FIGS. 10, 11, and 12, the distal end of the inner catheter extends into the distal portion of the outer catheter and extends distally beyond the outer catheter distal end.

In an embodiment, the outer catheter and/or the inner catheter, are configured to have variable flexibility, independently, along at least a portion of a longitudinal dimensions thereof. The variable flexibility allows for flexibility and/or kink resistance during the operation of the device.

In an embodiment, either or both of the catheters, independently, includes a plurality of portions with different stiffness values. In an embodiment, the stiffness of a relatively distal portion is less than the stiffness of a portion immediately proximal thereto.

The transition of the stiffness from a proximal portion to a distal portion (decreasing in stiffness or increasing in flexibility) for each catheter (inner or outer), independently, may be achieved by one or more ways, including, but not limited to: distal taper construction, forming the variable stiffness catheter from different material along its length, varying the thickness of the material forming the various portions, or presence or absence of additional elements (e.g., collars, layers) on a particular portion. The plurality of portions may be formed separately and then fixedly joined to one another, or may be integrally formed with one another during the construction of the catheter, for example, during extrusion or molding process.

In an embodiment, either or both of the catheters, independently, may include a proximal, an intermediate, and a distal elongate member, joined to one another by suitable means; a distal member having a lower stiffness than a member immediately proximal thereto or in the alternative a proximal member having a higher stiffness than a member immediately distal thereto.

In some embodiments, either or both of the catheters, independently, may have a proximal portion formed from material having a flexural modulus in a range from about 9,000 psi to about 250,000 psi.

In some embodiments, either or both of the catheters, independently, may have an intermediate portion formed from material having a flexural modulus in a range from about 600 psi to about 20,000 psi.

In some embodiments, either or both of the catheters, independently, may have a distal portion formed from material having a flexural modulus in a range from about 200 psi to 1,200 psi.

In some embodiments, stiffness ratio (distal portion:proximal portion) between any two adjacent variable stiffness portions may range from 0.03 to 0.8, 0.3 to 0.8, at least 0.03, at least 0.3, or at least 0.7.

Figure 15A:
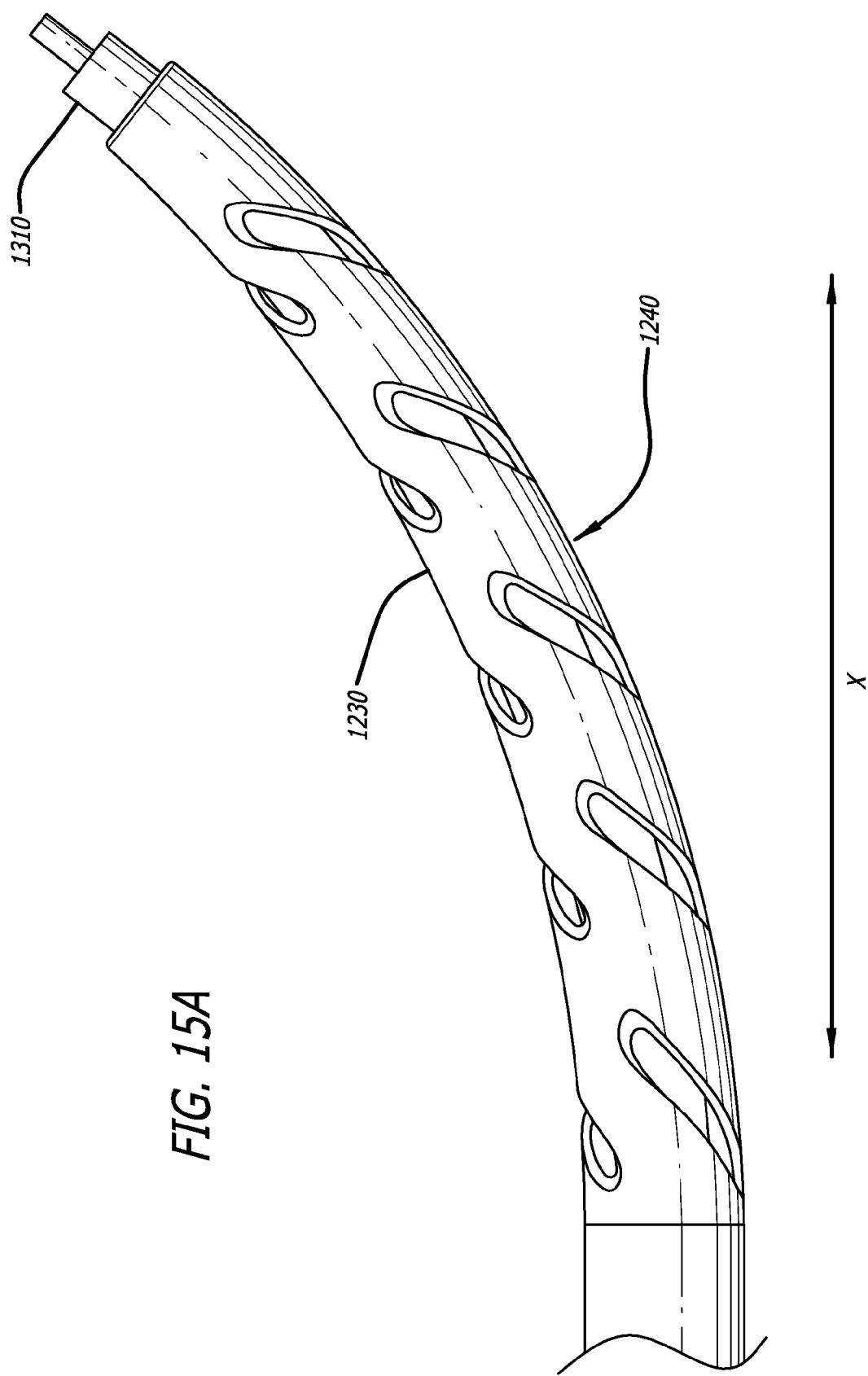
FIGS. 15A and 15B are illustrations of different embodiments of the distal end of the neuronal protection device of FIG. 10 shown in flexed configuration.

Now referring to FIG. 15A, the distal portion of the perfusion device 1200 including the distal portion of the outer catheter 1210 and inner catheter 1310, and earlier shown in FIG. 11A, is shown in a flexed configuration, having a curved distal portion.

Figure 15B:
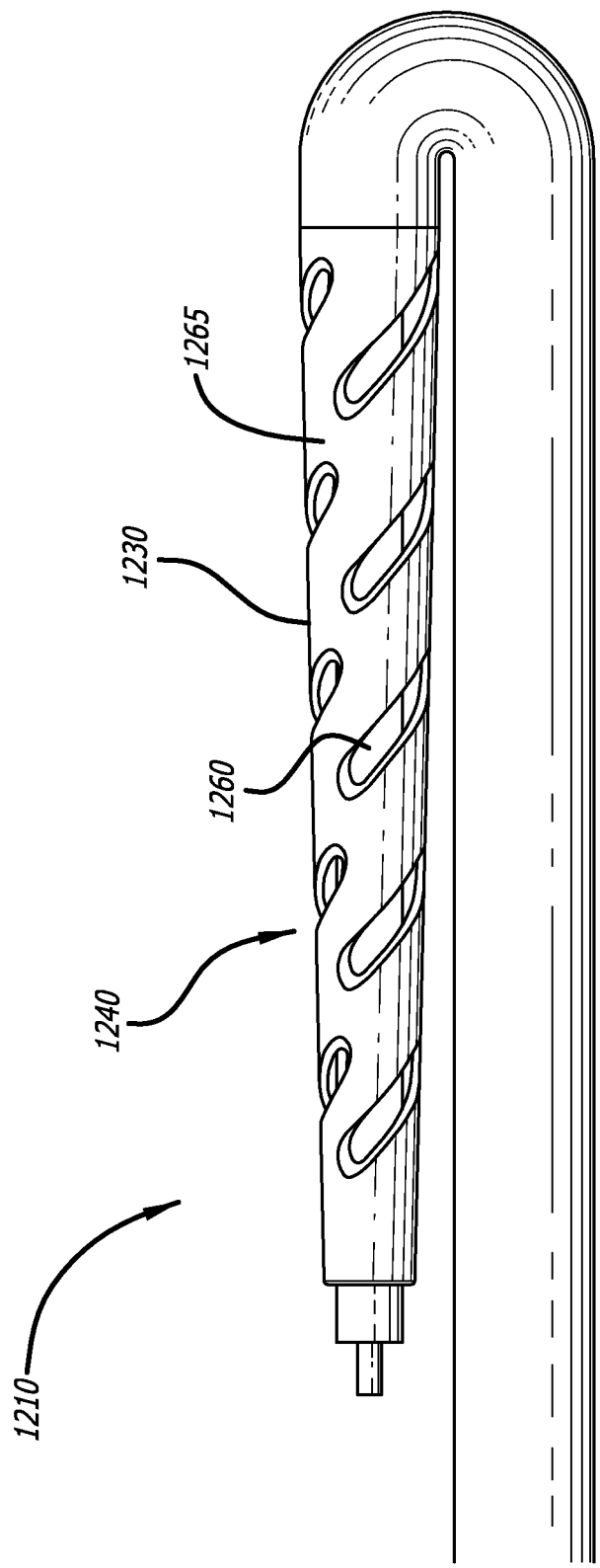

In an embodiment, and as shown in FIG. 15B, the neuronal protection device or NPS (e.g., 1200) including the outer catheter, inner catheter, and guidewire, is sufficiently flexible to bend, at its tapered distal portion, to provide an angle up to about 180 degrees, relative to the catheter in the unbent and straightened configuration. This configuration allows the NPS, in operation, to navigate the intracranial portions of the internal carotid artery that have a 180 degree bend. In an embodiment, the tapered distal portion configured to provide such a bend angle, has a length sufficiently long to navigate the cavernous section of the internal carotid artery. In an embodiment, the distal portion is configured to bend back on itself (e.g., about 180 degrees) over a distance of at least or about 10 mm. In an embodiment, the portion of the tapered distal portion configured to provide such a bend, is the distal end. In an embodiment, the distal end, of the device, normally the entire distal end, is configured to provide a bend angle of at least or about 180 over a distance of at least or about 10 mm. In an embodiment, and in operation, the NPS, in the bent configuration, at its distal end, may have a bend radius of at least or about 10 mm. In an embodiment, and in operation, the outer catheter, in the bent configuration, at its distal end, may have a bend radius of at least or about 10 mm.

Figure 16A:
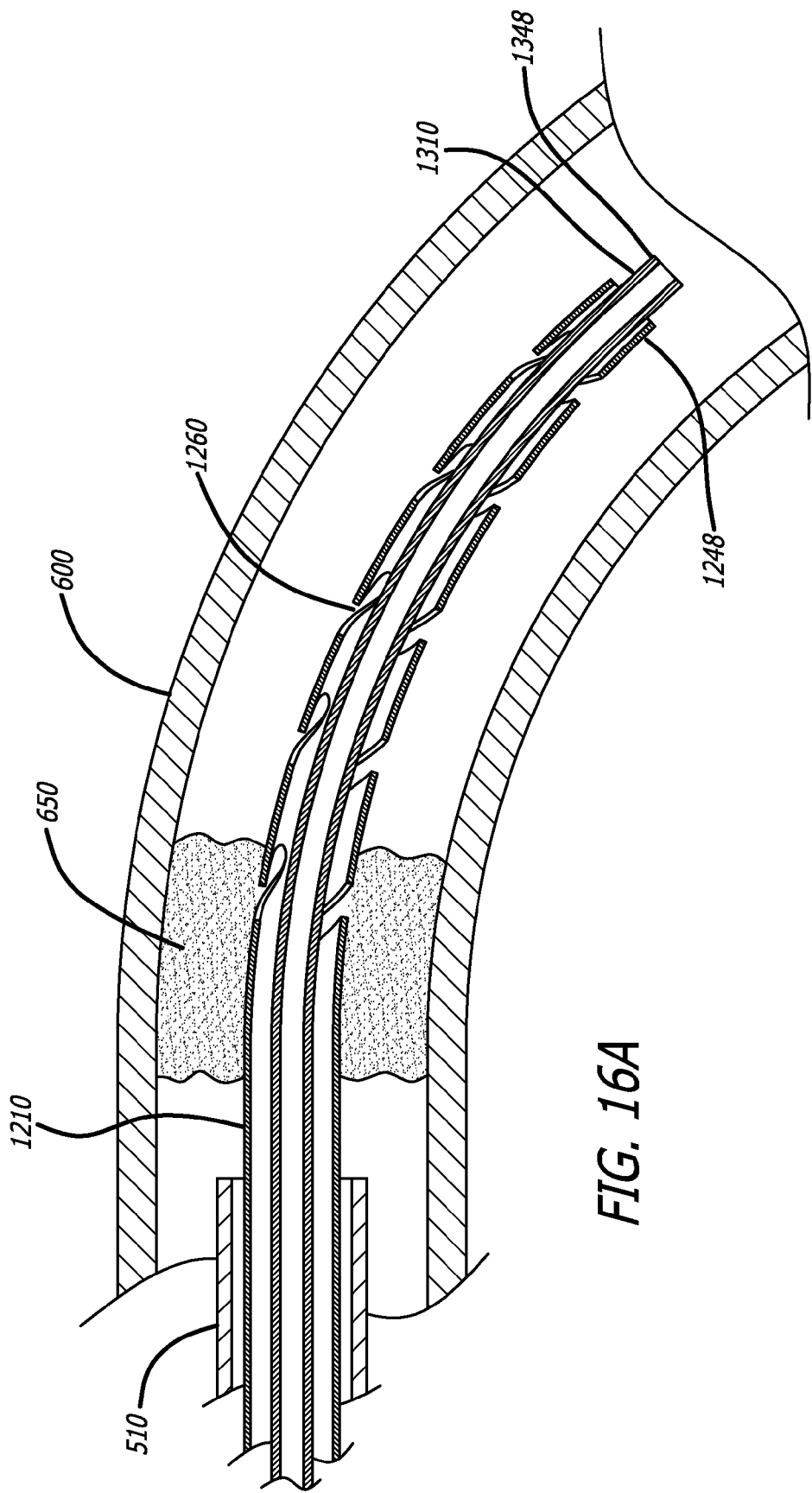
FIG. 16A is illustration of the flexed distal end of the neuronal protection device of FIG. 15 disposed in a patient's lumen with the outer catheter and inner catheter distal ends disposed distal to a thrombus site.
Figure 16B:
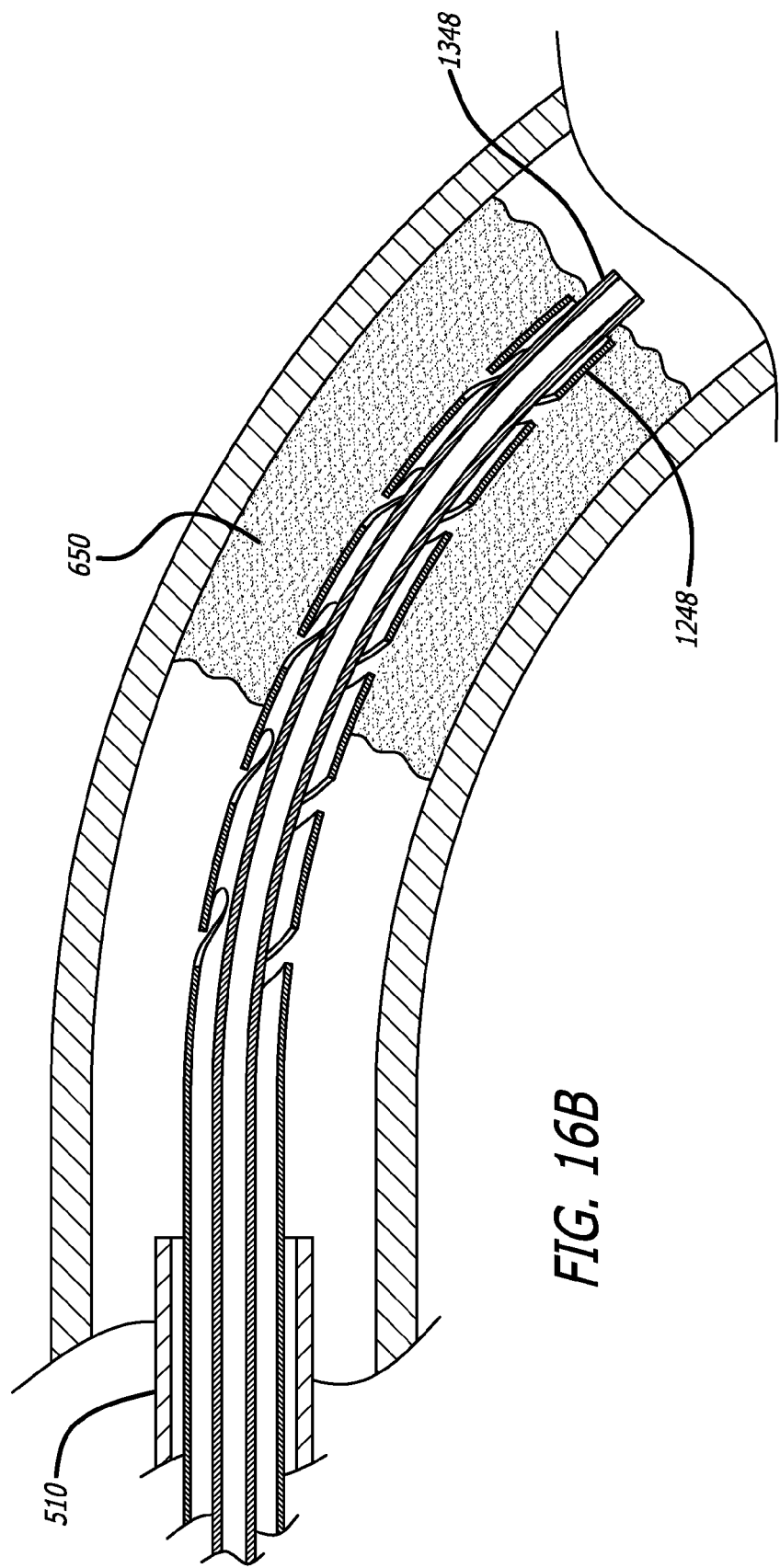
FIG. 16B is illustration of the flexed distal end of the neuronal protection device of FIG. 15 disposed in a patient's lumen with the inner catheter distal end disposed distal to the thrombus site and the distal end of the outer catheter disposed within or proximal to the thrombus site.

Now referring to FIG. 16, the distal portion of the perfusion device 200 is shown, in a flexed configuration, including the inner catheter 1310 slidably engaged inside the inner lumen 1250 of the outer catheter 1210 and extending distally from the distal tip 1248 of the outer catheter. In operation, the perfusion device tracks over the guidewire previously positioned within the patient. Upon proximal withdrawal of the guidewire and enabling fluid flow through the inner lumen of the inner catheter blood (or other fluids) may be perfused distal to the clot. The outer catheter and the desired flexing of its distal end controls the curvature of the inner catheter by providing constraining limits (e.g., the inner catheter cannot optimally flex beyond the distal tip of the outer catheter) in the flexed configuration allowing for better conformity to, and navigating within, the major arteries at the base of the brain. In an embodiment, this configuration enables less reliance on catheter tip durometer (hardness), allowing the device to bend more easily while still allowing for good column strength to aide in crossing the clot.

The inner catheter 1310 is configured for removably sliding within the inner lumen 1250 of the outer catheter. In some embodiments, in operation, any one or more of the following may be practiced according to the methods embodying features of the present invention: perfusion of blood or other solution (e.g., thrombolytic agents) through either the outer catheter or the inner catheter alone; perfusion of blood, TPA, or other solution/s simultaneously through both the inner and outer catheters; or as shown by way of example in FIG. 16B, perfusion of blood through the inner catheter with the inner catheter distal tip 1348 placed distal to the clot 650 while simultaneously infusing tissue plasminogen activator ("TPA) or other thrombolytic agent/s through the outer catheter 1210 with its distal tip 1248 positioned substantially or entirely in the clot 650. The apertures 1260 in the outer catheter allow for larger uninterrupted contact between TPA or other thrombolytic agents, with the clot, potentially increasing the effectiveness of the agents.

In an embodiment, and in operation, the neuronal protection device or NPS (e.g., 1200) including the outer catheter, inner catheter, and guidewire; as it navigates the intracranial portions of the internal carotid artery bends at the distal portion thereof, at an angle up to about 180 degrees, relative to the catheter in the unbent and straightened configuration. In an embodiment, the tapered distal portion configured to provide such a bend angle, has a length sufficiently long to navigate the cavernous section of the internal carotid artery. In an embodiment, the distal portion is configured to bend back on itself (e.g., about 180 degrees) over a distance of at least or about 10 mm. In an embodiment, the portion of the tapered distal portion configured to provide such a bend, is the distal end. In an embodiment, the distal end, of the device, normally the entire distal end, is configured to provide a bend angle of at least or about 180 over a distance of at least or about 10 mm. In an embodiment, and in operation, the NPS, in the bent configuration, at its distal end, may have a bend radius of at least or about 10 mm. In an embodiment, and in operation, the outer catheter, in the bent configuration, at its distal end, may have a bend radius of at least or about 10 mm. In an embodiment, as the outer catheter distal tip is flexed, the surface on the inside of the bend is in compression, and the surface on the outside is in tension. The width of the apertures located along the inside of the bend will decrease, and the width of the apertures located along the outside of the bend will increase, thereby relying less on the material properties in tension and compression and more on the geometry of the apertures and their placement along the tapered tip.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although embodiments of the invention have been described in substantial detail with reference to one or more specific embodiments, those of ordinary skill in the art will recognize that changes may be made to the embodiments specifically disclosed in this application, yet these modifications and improvements are within the scope and spirit of the invention.

Embodiments illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the invention claimed. The term "a" or "an" can refer to one of or a plurality of the elements it modifies (e.g., "a reagent" can mean one or more reagents) unless it is contextually clear either one of the elements or more than one of the elements is described. Thus, it should be understood that although embodiments have been specifically disclosed by representative embodiments and optional features, modification and variation of the concepts herein disclosed may be resorted to by those skilled in the art, and such modifications and variations are considered within the scope of this invention.

Certain embodiments of the invention are set forth in the claim(s) that follow(s).

That which is claimed:

1. An assembly for cerebral perfusion therapy, including:
    an outer catheter configured for cerebral perfusion therapy and including
        a single lumen first elongate member having a proximal portion with a proximal end, a distally tapered distal portion having a distally tapered distal end and an open distal tip, the tapered distal end configured to facilitate navigating the outer catheter into the cerebral circulation and traversing clots within vessels within the brain, an inner lumen extending along at least the distal portion, a plurality of oblong apertures disposed along the distal end and extending from an outer surface of the first elongate member to the first elongate member inner lumen, the apertures having a first transverse dimension and a second transverse dimension which is substantially perpendicular to the first transverse dimension and substantially less than the first transverse dimension;
        the outer catheter configured for perfusion of fluids including any one or more of blood, therapeutic agents, diagnostic agents, or lytic solutions; through or in the vicinity of an obstructing cerebral thrombus;
        the outer catheter configured to bend over a range up to 180 degrees relative to the catheter in an unbent and straight configuration; and
    An inner catheter configured for use in cerebral perfusion therapy and including
        a second elongate member having a proximal portion with a proximal end, a distal portion with a distal end and an open distal tip, a lumen extending along at least the distal portion, the inner catheter configured for slidable coaxial advancement within the inner lumen of the outer catheter and slidable disposal at any one or more locations, proximal, adjacent, or distal; to at least a portion of the apertures; the inner catheter further being configured for extending distally from the open distal tip of the outer catheter.

2. An assembly according to claim 1, wherein the outer catheter has a variable stiffness along a length thereof.

3. An assembly according to claim 2, wherein the stiffness of a relatively distal portion of the outer catheter is less than the stiffness of a portion relatively proximal thereto.

4. An assembly according to claim 1, wherein the bend is over a distance of at least 10 mm.

5. An assembly according to claim 1, wherein the inner catheter has a variable stiffness along a length thereof.

6. An assembly according to claim 5, wherein the stiffness of a relatively distal portion of the inner catheter is less than the stiffness of a portion relatively proximal thereto.

7. An assembly according to claim 1, wherein the sum of the areas of the apertures is at least the same as an inner diameter of the outer catheter at a location proximal to a proximal end of the distal tapered portion of the outer catheter.

8. An assembly according to claim 1, wherein the sum of the areas of the apertures is greater than an inner diameter of the outer catheter at a location proximal to a proximal end of the distal tapered portion of the outer catheter.

9. An assembly according to claim 1, wherein, the apertures are configured to provide for a fluid flow direction having an acute angle as measured from the surface of the outer catheter distal end.

10. An assembly according to claim 1, wherein the inner catheter is further configured for delivery of either or both fluids including blood, therapeutic agents, diagnostic agents, lytic solutions and the like; and delivery of treatment devices including thrombectomy devices; to or in the vicinity of the obstructing thrombus.

11. A method for cerebral perfusion therapy of a patient, including:
    Providing a cerebral perfusion device including
        An outer catheter configured for cerebral perfusion therapy and including a single lumen first elongate member having a proximal portion with a proximal end, a distally tapered distal portion having a distally tapered distal end and an open distal tip, the tapered distal end configured to facilitate navigating the outer catheter into the cerebral circulation and traversing clots within vessels within the brain, an inner lumen extending along at least the distal portion, a plurality of oblong apertures disposed along the distal portion and extending from an outer surface of the first elongate member to the first elongate member inner lumen, the apertures having a first transverse dimension and a second transverse dimension which is substantially perpendicular to the first transverse dimension and substantially less than the first transverse dimension;
        the outer catheter configured for perfusion of fluids including any one or more of blood, therapeutic agents, diagnostic agents, or lytic solutions; through or in the vicinity of an obstructing cerebral thrombus; and An inner catheter configured for use in cerebral perfusion therapy and including a second elongate member having a proximal portion with a proximal end, a distal portion with a distal end and an open distal tip, a lumen extending along at least the distal portion, the inner catheter configured for slidable coaxial advancement within the inner lumen of the outer catheter and slidable disposal at any one or more locations, proximal, adjacent, or distal; to at least a portion of the apertures; the inner catheter further being configured for extending distally from the open distal tip of the outer catheter;

the cerebral perfusion device configured to bend over a range up to 180 degrees relative to the catheter in an unbent and straight configuration;

Providing a perfusion pump fluidically connectable to the cerebral perfusion device and configured to actively supply blood to a treatment site through the outer catheter or the inner catheter;

Advancing intracorporeally the outer catheter and the inner catheter through a patient's artery to a treatment site distal to a distal edge of the thrombus site;

Retracting the inner catheter proximally to expose at least a portion of the apertures which are distal to the distal edge of the thrombus site; and Pumping blood from the perfusion pump through either the outer catheter or the inner catheter to the treatment site distal to the thrombus site, through any one or more of the open distal tip of the outer catheter, the open distal tip of the inner catheter, and any unobstructed apertures.

12. A method according to claim 11, wherein the advancing step comprises advancing intracorporeally the outer catheter and the inner catheter through an cavernous section of an internal carotid artery.

13. A method according to claim 11, wherein the bend is over a distance of at least 10 mm.

14. A method according to claim 11, wherein the bend is over a distance of at least or about 10 mm as the device navigates through an cavernous section of an internal carotid artery.

15. A method according to claim 11, wherein the sum of the areas of the apertures is at least the same as an inner diameter of the outer catheter at a location proximal to a proximal end of the distal tapered portion of the outer catheter.

16. A method according to claim 11, further including advancing a revascularizing device including an endovascular thrombectomy device through the inner lumen of the inner catheter and revascularizing the thrombus site.

17. A method according to claim 16, wherein the revascularization step includes advancing an endovascular thrombectomy device through the inner catheter and performing a thrombectomy procedure.

18. A method according to claim 17, wherein the method is to directly treat ischemic stroke.

\* \* \* \* \*